(12) United States Patent
Alvaro et al.

(10) Patent No.: US 7,189,713 B2
(45) Date of Patent: Mar. 13, 2007

(54) PIPERIDINE DERIVATIVES

(75) Inventors: Giuseppe Alvaro, Verona (IT); Romano Di Fabio, Verona (IT); Maria Elvira Tranquillini, Verona (IT); Simone Spada, Verona (IT)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 10/502,255

(22) PCT Filed: Feb. 10, 2003

(86) PCT No.: PCT/EP03/01308

§ 371 (c)(1),
(2), (4) Date: Mar. 28, 2005

(87) PCT Pub. No.: WO03/066635

PCT Pub. Date: Aug. 14, 2003

(65) Prior Publication Data

US 2005/0176715 A1  Aug. 11, 2005

(30) Foreign Application Priority Data

Feb. 8, 2002 (GB) .................. 0203020.3

(51) Int. Cl.
*A61K 31/535* (2006.01)
*A01N 43/58* (2006.01)
*C07D 498/00* (2006.01)
*C07D 265/12* (2006.01)
*C07D 471/00* (2006.01)

(52) U.S. Cl. ............... 514/230.5; 514/249; 544/91; 544/92; 544/279; 544/349

(58) Field of Classification Search ........... 514/249; 544/349, 279, 105
See application file for complete search history.

(56) References Cited

U.S. PATENT DOCUMENTS

| | | | |
|---|---|---|---|
| 4,087,424 A | 5/1978 | Saikawa et al. | |
| 4,110,327 A | 8/1978 | Saikawa et al. | |
| 4,112,090 A | 9/1978 | Saikawa et al. | |
| 4,219,554 A | 8/1980 | Saikawa et al. | |
| 4,308,387 A | 12/1981 | Bjork et al. | |
| 4,327,097 A | 4/1982 | Saikawa et al. | |
| 4,379,152 A | 4/1983 | Saikawa et al. | |
| 4,410,522 A | 10/1983 | Saikawa et al. | |
| 5,028,610 A | 7/1991 | Hirai et al. | |
| 5,109,014 A | 4/1992 | Jacobson et al. | |
| 5,334,606 A | 8/1994 | MacLeod et al. | |

(Continued)

FOREIGN PATENT DOCUMENTS

DE   2519400   4/1978

(Continued)

OTHER PUBLICATIONS

Challet, E., et al. Neuropharmacology 40(3):408-415 (2001).

(Continued)

*Primary Examiner*—Zachary C. Tucker
(74) *Attorney, Agent, or Firm*—Lorie Ann Morgan

(57) ABSTRACT

The present invention relates to piperidine derivatives of formula (I):

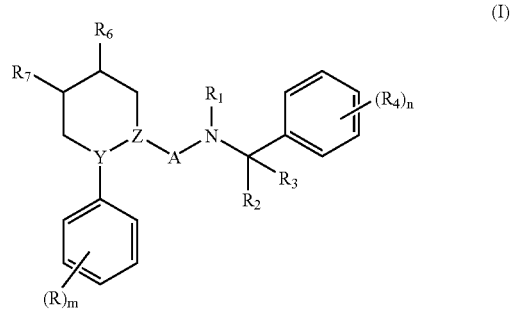

R represents halogen or $C_{1-4}$ alkyl
$R_1$ represents $C_{1-4}$ alkyl;
$R_2$ or $R_3$ independently represent hydrogen or $C_{1-4}$ alkyl;
$R_4$ represents trifluoromethyl, $C_{1-4}$ alkyl, $C_{1-4}$ alkoxy, trifluoromethoxy or halogen;
$R_5$ represents hydrogen, $C_{1-4}$ alkyl or $C_{3-7}$ cycloalkyl;
$R_6$ is hydrogen and $R_7$ is a radical of formula (W):

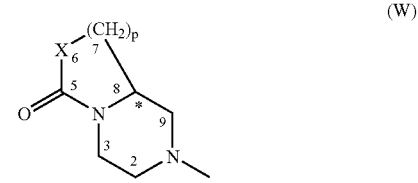

or $R_6$ is a radical of formula (W) and $R_7$ is hydrogen;
X represents $CH_2$, $NR_5$ or O;
Y represents Nitrogen and Z is CH or Y represents CH and Z is Nitrogen;
A represents C(O) or S(O)q, provided that when Y is nitrogen and Z is CH, A is not $S(O)_q$;
m is zero or an integer from 1 to 3;
n is an integer from 1 to 3;
p and q are independently an integer from 1 to 2;
and pharmaceutically acceptable salts and solvates thereof.

The process for their preparation and their use in the treatment of a condition mediated by tachykinins.

71 Claims, No Drawings

U.S. PATENT DOCUMENTS

| | | | |
|---|---|---|---|
| 5,348,955 A | 9/1994 | Greenlee et al. |
| 5,360,820 A | 11/1994 | Hagan et al. |
| 5,464,788 A | 11/1995 | Bock et al. |
| 5,538,982 A | 7/1996 | Hagan et al. |
| 5,563,127 A | 10/1996 | Amparo et al. |
| 5,576,317 A | 11/1996 | Gonsalves et al. |
| 5,696,123 A | 12/1997 | Dollinger et al. |
| 5,698,538 A | 12/1997 | Amparo et al. |
| 5,708,006 A | 1/1998 | Dollinger et al. |
| 5,710,169 A | 1/1998 | Russell et al. |
| 5,716,942 A | 2/1998 | Dorn et al. |
| 5,756,504 A | 5/1998 | Bock et al. |
| 5,814,636 A | 9/1998 | Katano et al. |
| 5,859,015 A | 1/1999 | Graham et al. |
| 5,883,096 A | 3/1999 | Lowe et al. |
| 5,935,951 A | 8/1999 | Ofner et al. |
| 5,952,315 A | 9/1999 | Baker et al. |
| 5,977,104 A | 11/1999 | Baker et al. |
| 5,985,881 A | 11/1999 | Dollinger et al. |
| 5,998,444 A | 12/1999 | Russell et al. |
| 6,037,352 A | 3/2000 | Lowe et al. |
| 6,057,323 A | 5/2000 | Zhang et al. |
| 6,090,807 A | 7/2000 | Hellendahl et al. |
| 6,114,315 A | 9/2000 | Baker et al. |
| 6,117,855 A | 9/2000 | Carlson et al. |
| 6,147,083 A | 11/2000 | Russell et al. |
| 6,191,135 B1 | 2/2001 | Dollinger et al. |
| 6,191,139 B1 | 2/2001 | Hagan et al. |
| 6,197,772 B1 | 3/2001 | Janssens et al. |
| 6,235,732 B1 | 5/2001 | Dollinger et al. |
| 6,288,068 B1 | 9/2001 | Lowe et al. |
| 6,319,953 B1 | 11/2001 | Carlson et al. |
| RE37,886 E | 10/2002 | Janssens et al. |
| 6,521,621 B1 | 2/2003 | Janssens et al. |
| 6,642,240 B2 | 11/2003 | Alvaro et al. |
| 2002/0103205 A1 | 8/2002 | Lowe et al. |

FOREIGN PATENT DOCUMENTS

| | | |
|---|---|---|
| EP | 287734 | 10/1987 |
| EP | 293532 | 10/1987 |
| EP | 0532456 | 3/1993 |
| EP | 0655442 | 5/1995 |
| EP | 718287 | 12/1995 |
| EP | 0721941 | 7/1996 |
| EP | 1-326 632 A | 7/2003 |
| GB | 1508062 | 4/1975 |
| JP | 57/118587 | 7/1982 |
| WO | WO 92/16111 | 10/1992 |
| WO | WO 95/00498 | 1/1995 |
| WO | WO 95/25443 | 9/1995 |
| WO | WO 96/02503 | 2/1996 |
| WO | WO 96/03378 | 2/1996 |
| WO | WO 96/10562 | 4/1996 |
| WO | WO 96/14844 | 5/1996 |
| WO | WO 96/20173 | 7/1996 |
| WO | WO 97/16440 | 5/1997 |
| WO | WO 97/24324 | 7/1997 |
| WO | WO 97/32865 | 9/1997 |
| WO | WO 97/36592 | 10/1997 |
| WO | WO 97/36593 | 10/1997 |
| WO | WO 97/36888 | 10/1997 |
| WO | WO 97/36889 | 10/1997 |
| WO | WO 98/01133 | 1/1998 |
| WO | WO 98/20001 | 5/1998 |
| WO | WO 98/57954 | 12/1998 |
| WO | WO 99/09985 | 3/1999 |
| WO | WO 99/26921 | 6/1999 |
| WO | WO 99/37304 | 7/1999 |
| WO | WO 01/25219 | 4/2001 |
| WO | WO 02/00631 | 1/2002 |
| WO | WO 02/32867 | 4/2002 |
| WO | WO 02/032867 | 4/2002 |
| WO | WO 02/055518 | 7/2002 |
| WO | WO 02/057233 | 7/2002 |
| WO | WO 04/033428 | 4/2004 |
| WO | WO-04 091624 A | 10/2004 |

OTHER PUBLICATIONS

Davis, David T., "Synthesis A. Biological Activity of a Series of Piperazin-2, 3-Biones," Journal of Antibiotics, vol. XLII, No. 3, 1989, pp. 367-373.

Megens, A., et al. J. Pharmacology and Experimental Therapeutics 302(2):696-709 (2002).

Pacher, P., et al. "Review of Cardiovascular Effects of Fluoxetine, A Selective Serotonine Reuptake Inhibitor, Compared to Tricyclic Antidepressants." Current Medicinal Chemistry, 5, pp. 381-390, 1998.

Romerio, et al. Clinical Pharmacology and Therapeutics 66(5):522-527 (1999).

Rupniak et al. "Differential inhibition of foot tapping and chromodacyorrhoea in gerbils by CNS penetrant and non-penetrant tachykinin NK, receptor antagonists." European Journal of Pharmacology 265:179-183 (1994).

Giardina G.A.M., et al; Recent advances in neurokinin-3 receptor antagonists.: Expert Opinion On-Therapeutic Patients; 2000. 10(6); 939-960; Ashley Publications; GB.

Acute Stress Disorder; Diagnostic and Statistical Manual of Mental Disorders (DSM-IV); 2000; Fourth Edition; pp. 469-472; American Psychiatric Association; Washington, DC, USA.

Anxiety Disorders; Diagnostic and Statistical Manual of Mental Disorders (DSM-IV); 2000; Fourth Edition; 429-30; American Psychiatric Association; Washington, DC, USA.

Argyropoulos, et al.; Exp. Opin. Invest. Drugs; 2000; 9/6; 1871-1876.

Ballard, et al.; European Journal of Pharmacology; 2001; 412; 266-284.

Kramer et al.; Science; 1998; 281; 1640-1646.

Scrima, et al.; Biol Psychiatry; 1989; 26; 331-343.

Sleep disorders; Diagnostic and Statistical Manual of Mental Disorders (DSM-IV); 2000; Fourth Edition; 597-661; American Psychiatric Association; Washington, DC, USA.

PIPERIDINE DERIVATIVES

CROSS REFERENCE TO RELATED APPLICATION

This application is a 371 Application of PCT/EP03/01308. filed 10 Feb. 2003, which claims priority to GB Application Serial No. 0203020.3, filed 8 Feb. 2002.

The present invention relates to diazabicycle derivatives, to processes for their preparation, to pharmaceutical compositions containing them and to their medical use.

In particular, the invention relates to novel compounds which are potent and specific antagonists of tachykinins, including substance P and other neurokinins.

Thus, the present invention provides compounds of formula (I)

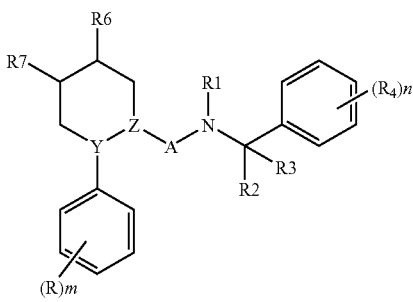

(I)

R represents halogen or $C_{1-4}$ alkyl;
$R_1$ represents $C_{1-4}$ alkyl;
$R_2$ or $R_3$ independently represent hydrogen or $C_{1-4}$ alkyl;
$R_4$ represents trifluoromethyl, $C_{1-4}$ alkyl, $C_{1-4}$ alkoxy, trifluoromethoxy or halogen;
$R_5$ represents hydrogen, $C_{1-4}$ alkyl or $C_{3-7}$ cycloalkyl;
$R_6$ is hydrogen and $R_7$ is a radical of formula (W):

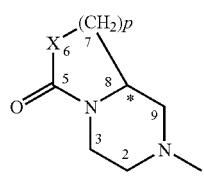

(W)

or $R_6$ is a radical of formula (W) and $R_7$ is hydrogen;
X represents $CH_2$, $NR_5$ or O;
Y represents Nitrogen and Z is CH or Y represents CH and Z is Nitrogen;
A represents C(O) or S(O)q, provided that when Y is nitrogen and Z is CH, A is not S(O)q;
m is zero or an integer from 1 to 3;
n is an integer from 1 to 3;
p and q are independently an integer from 1 to 2;

and pharmaceutically acceptable salts and solvates thereof.

A further embodiment of the invention is

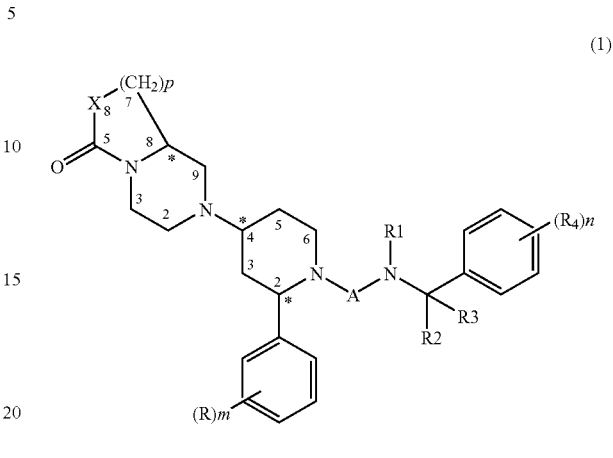

(1)

wherein
A represents C(O) or S(O)q;
X represents $CH_2$, $NR_5$ or O;
R represents halogen atom or $C_{1-4}$ alkyl;
$R_1$ represents a $C_{1-4}$ alkyl group;
$R_2$ or $R_3$ independently represent hydrogen or $C_{1-4}$ allyl;
$R_4$ represents trifluoromethyl, $C_{1-4}$ alkyl, $C_{1-4}$ alkoxy, trifluoromethoxy or a halogen;
$R_5$ represents hydrogen, $C_{1-4}$ alkyl or $C_{3-7}$ cycloalkyl;
m is zero or an integer from 1 to 3;
n is an integer from 1 to 3;
p or q are independently an integer from 1 to 2;

and pharmaceutically acceptable salts and solvates thereof.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, trifluoroacetates, lactates, fumarates, malates and maleates.

The solvates may, for example, be hydrates.

References hereinafter to a compound according to the invention include both compounds of formula (I) and their pharmaceutically acceptable acid addition salts together with pharmaceutically acceptable solvates.

Suitable pharmaceutical acceptable salts of the compounds of general formula (I) may be obtained in a crystalline form and/or in an amorphous form or as a mixture thereof.

It will be appreciated by those skilled in the art that the compounds of formula (I) contain at least three chiral centres (namely the carbon atom shown as * in the formulae from 1a to 4h).

Thus, when $R_6$ is hydrogen, $R_7$ is a radical of formula (W), Z is nitrogen and Y is carbon, the chiral centres may be represented by the formulae (1a, 1b, 1c, 1d, 1e, 1f, 1g and 1h)

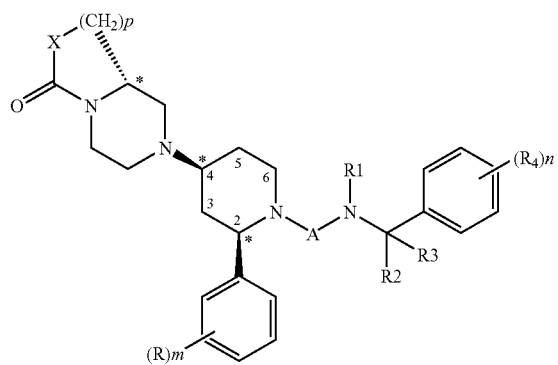
1a
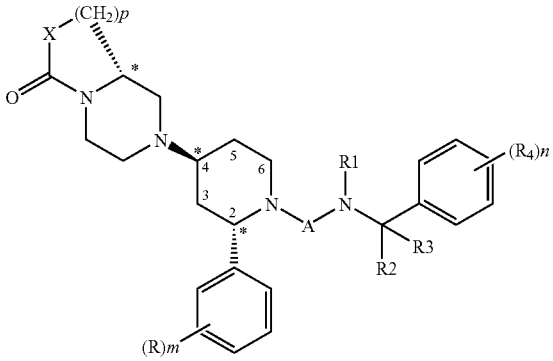
1e
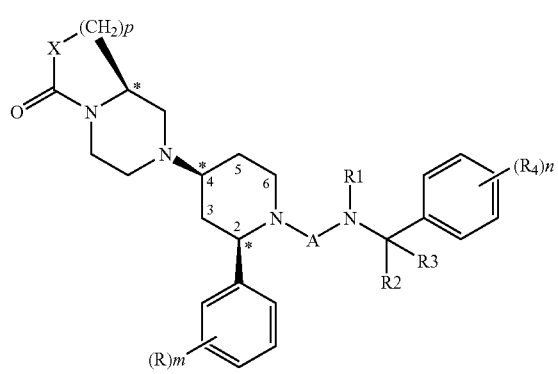
1b
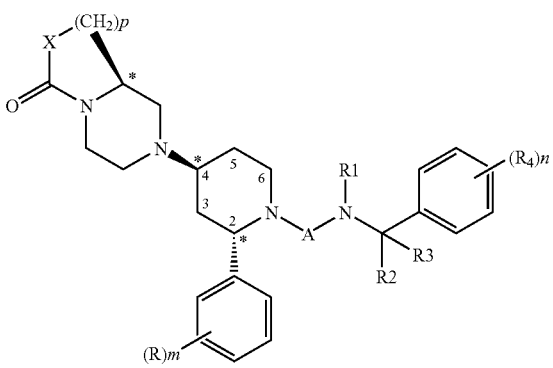
1f
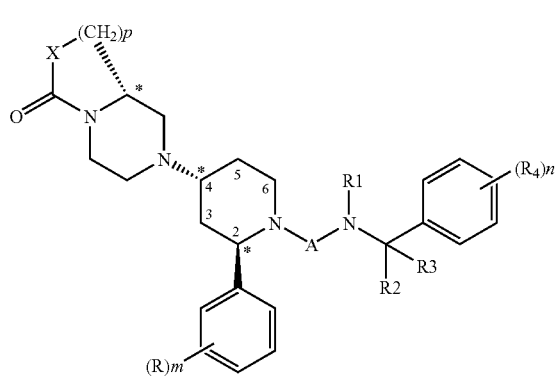
1c
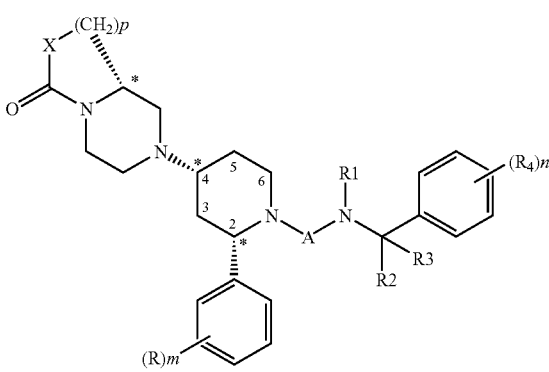
1g
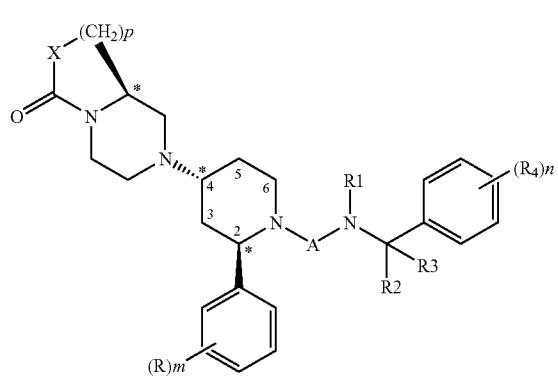
1d
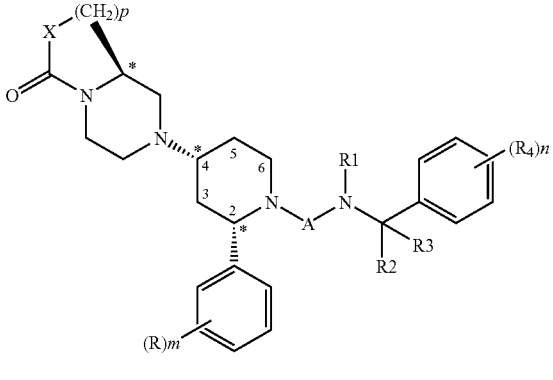
1h
When $R_7$ is hydrogen, $R_6$ is a radical of formula (W), Z is CH and Y is nitrogen, the chiral centres may be represented by the formulae (2a, 2b, 2c, 2d, 2e, 2f, 2g and 2h)

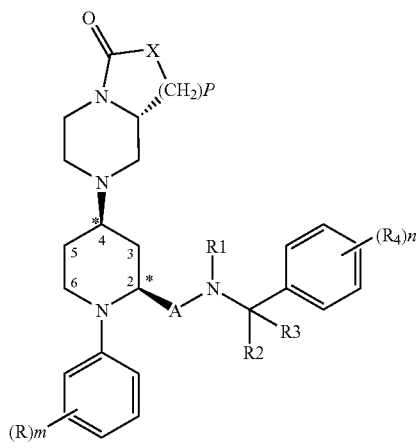
2a
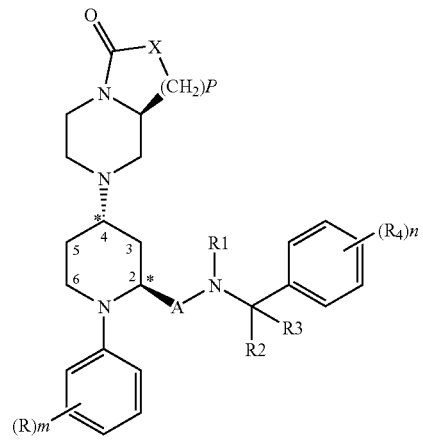
2d
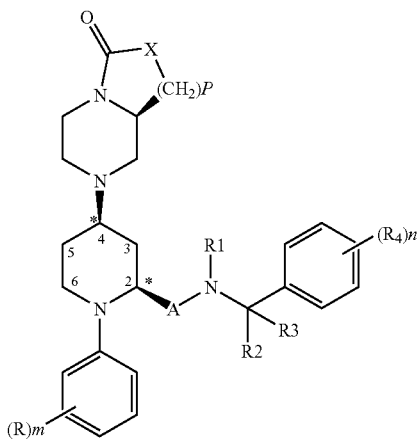
2b
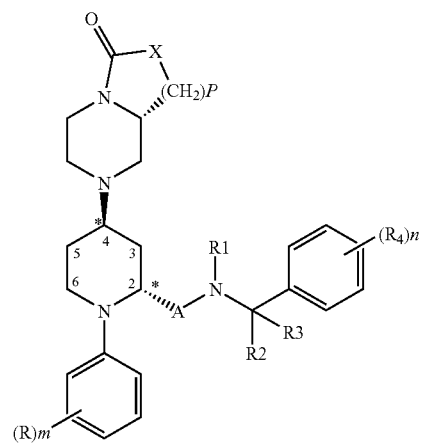
2e
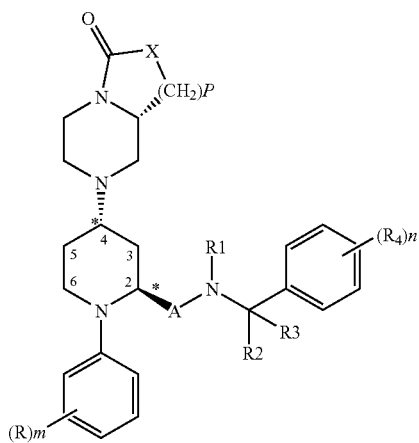
2c
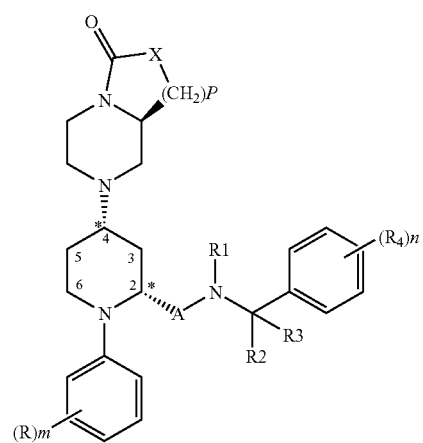
2f 2g
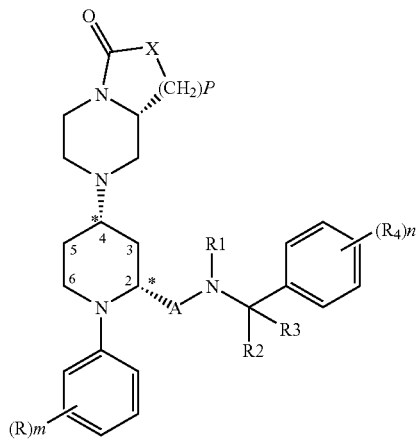
2h
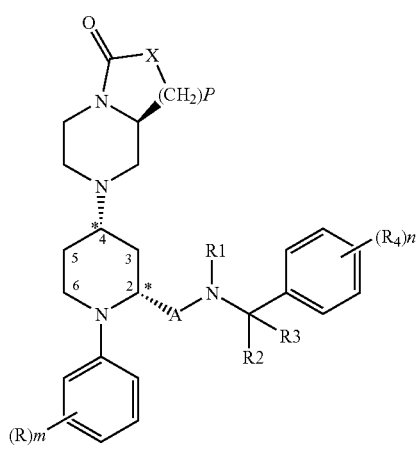
When R₆ is hydrogen, R₇ is a radical of formula (W, Z is CH and Y is nitrogen, the chiral centres may be represented by the formulae (3a, 3b, 3c, 3d, 3e, 3f, 3g and 3h)
3a
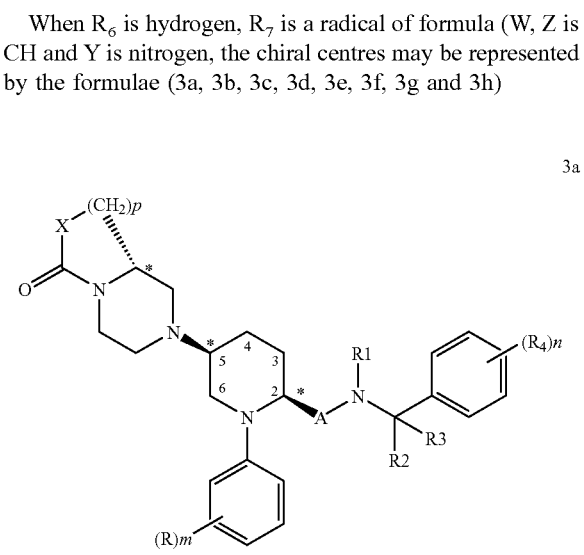
3b
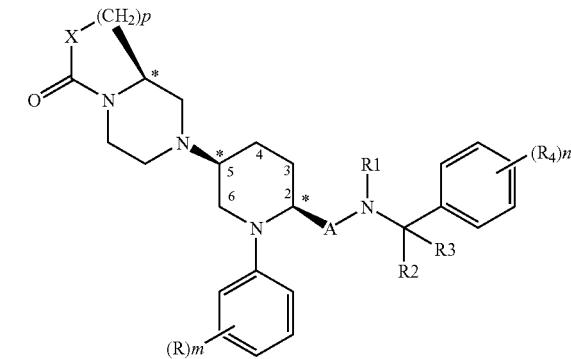
3c
3d
3e
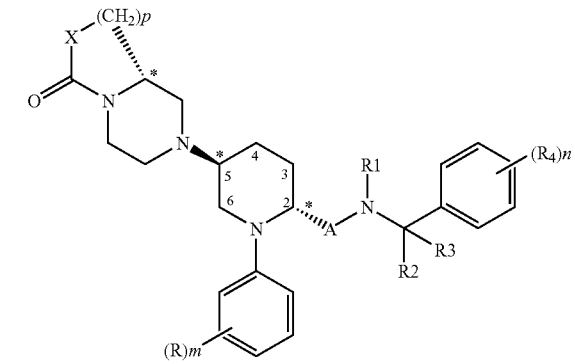

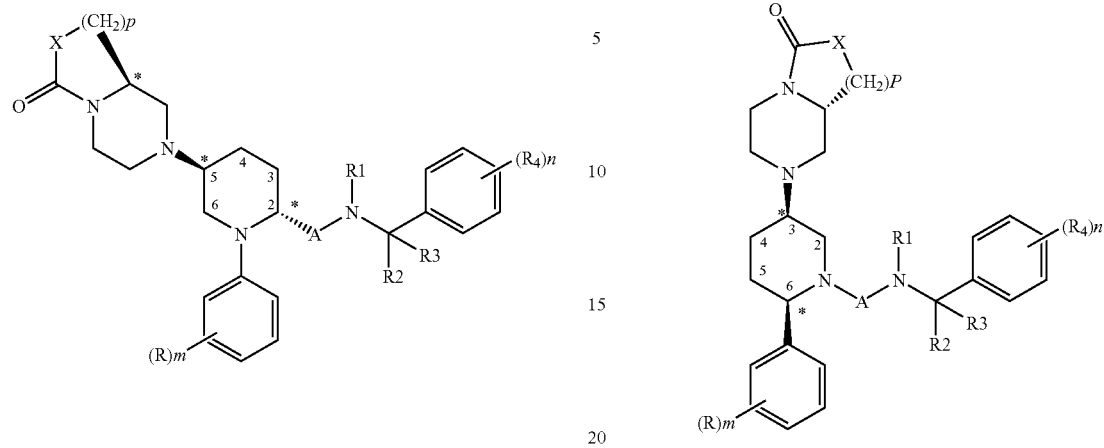
3f
3g
3h
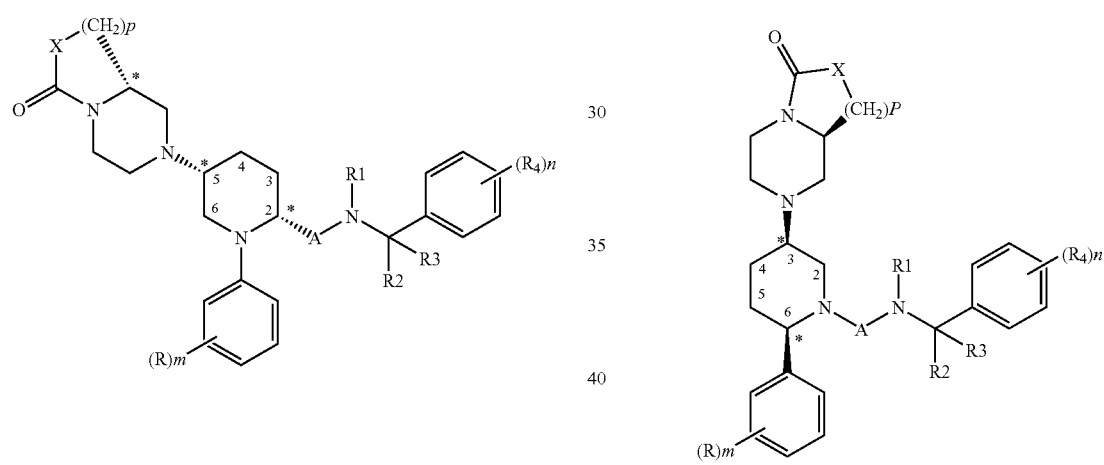
4a
4b
4c
When R₇ is hydrogen, R₆ is a radical of formula (W), Z is nitrogen and Y is carbon, the chiral centres may be represented by the formulae (4a, 4b, 4c, 4d, 4e, 4f, 4g and 4h)
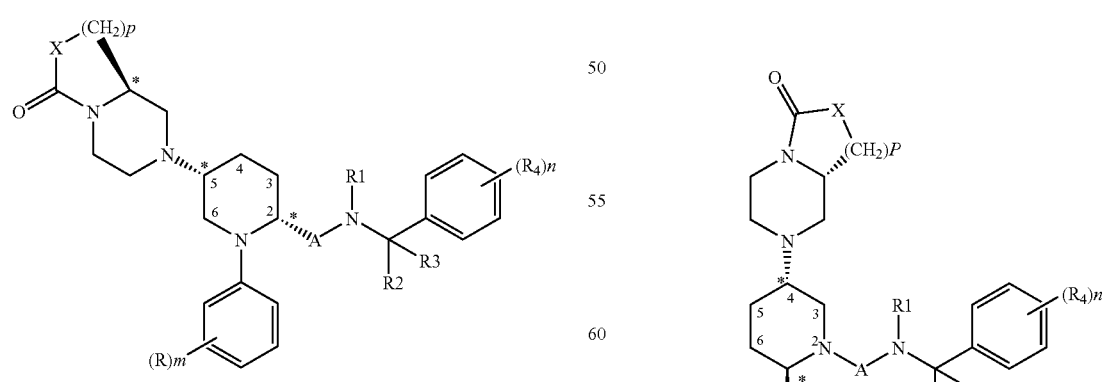

-continued

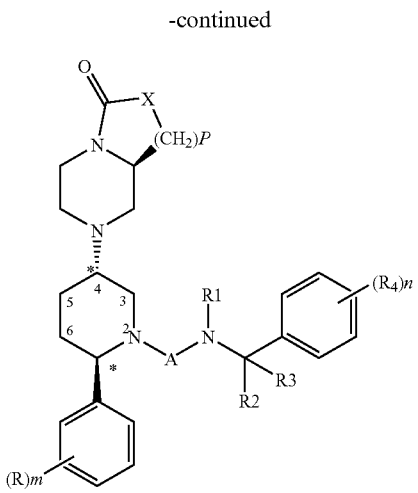
4d

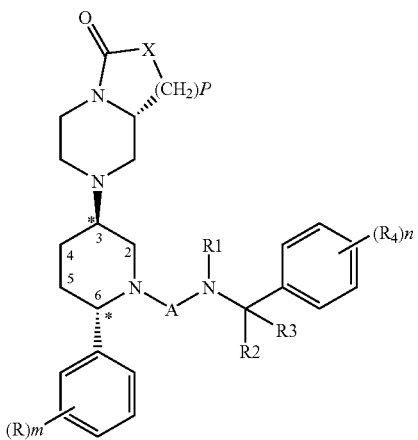
4e

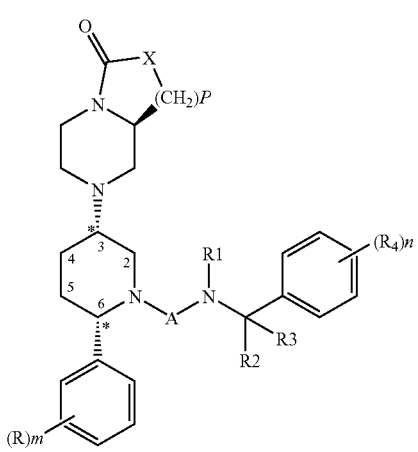
4f

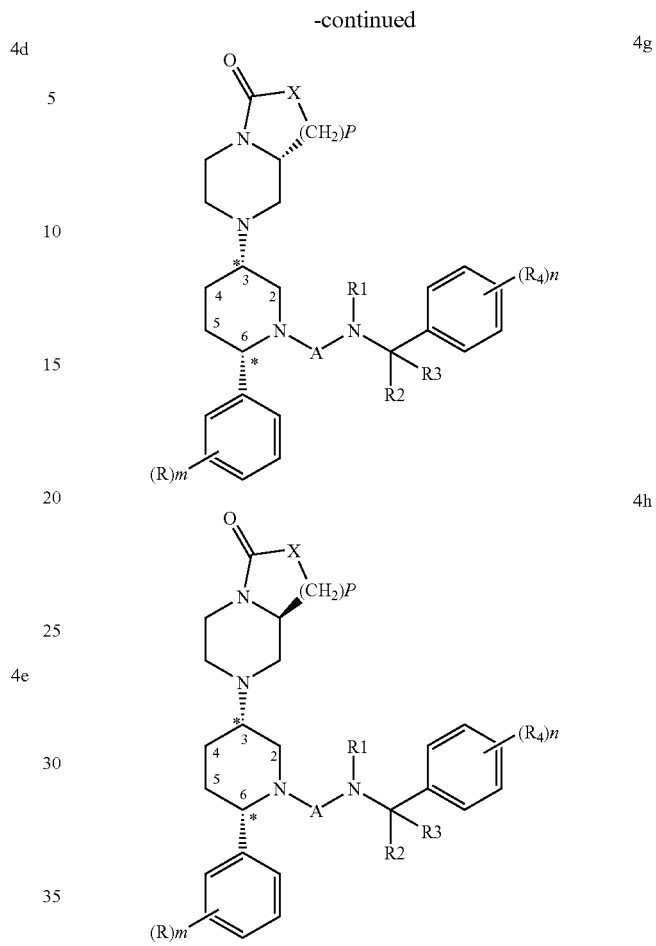

4g

4h

The wedge shaped bond indicates that the bond is above the plane of the paper and it is referred to as β configuration. The broken bond indicates that the bond is below the plane of the paper and is in the α configuration.

In the specific compounds named below when Y is CH and Z is Nitrogen, the β configuration at the 2 position of the piperidine ring corresponds to the R configuration and the β configuration at 4 position of the piperidine ring corresponds to the S configuration. The α configuration at the 2 position of the piperidine ring corresponds to the S configuration and the α configuration at 4 position of the piperidine ring corresponds to the R configuration.

In the specific compounds named below when Y is Nitrogen and Z is CH, the β configuration at the 2 position of the piperidine ring corresponds to the S configuration and the β configuration at 4 position of the piperidine ring corresponds to the S configuration. The α configuration at the 2 position of the piperidine ring corresponds to the R configuration and the α configuration at 4 position of the piperidine ring corresponds to the R configuration.

The assignment of the R or S configuration at the 2 and the 4 positions has been made according to the rules of Cahn, Ingold and Prelog, Experientia 1956, 12, 81.

The configuration of the chiral carbons atom of the piperidine ring shown in formulae from 1c to 1f, from 2c to 2f, from 3c to 3f and from 4c a 4f is hereinafter referred to as anti configuration and in formulae 1a, 1b, 1 g, 1 h, 2a, 2b, 2g, 2h, 3a, 3b, 3g, 3h, 4a, 4b, 4g and 4h as the syn configuration.

Further asymmetric carbon atoms are possible in the compounds of formula (I). Thus, when $R_2$ and $R_3$ are not the same group, the compounds of formula (I) possess at least four asymmetric carbon atoms.

It is to be understood that all stereoisomeric forms, including all enantiomers, diastereoisomers and all mixtures thereof, including racemates, are encompassed within the scope of the present invention and the reference to compounds of formula (I) includes all stereoisomeric forms unless otherwise stated.

Compounds (I) may be obtained as a crystalline form. Thus for example Compounds of formula(I) may be obtained as an anhydrous crystalline form or as a dihydrate crystalline form or a mixture thereof. It is to be understood that these crystalline forms or a mixture thereof are encompassed within the scope of the invention.

Furthermore, some of the crystalline forms of the compounds of structure (I) may exist as polymorphs, which are included in the present invention.

The present invention also includes isotopically-labelled compound. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography) and $^{125}I$ are particularly useful in SPECT (single photon emission computerized tomography), all useful in brain imaging. Furthermore, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) of this invention can generally be prepared by carrying out the procedures disclosed in the Schemes and/or in the Examples below by substituting a readily available isotopically labelled reagent for a non-isotopically labelled reagent.

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl or tert butyl.

The term $C_{1-4}$ alkoxy group may be a straight chain or a branched chain alkoxy group, for example methoxy, ethoxy, propoxy, prop-2-oxy, butoxy, but-2-oxy or methylprop-2-oxy.

The term halogen refers to a fluorine, chlorine, bromine or iodine atom.

The term $C_{3-7}$ cycloalkyl group means a non aromatic monocyclic hydrocarbon ring of 3 to 7 carbon atoms such as, for example, cyclopropyl, cyclobutyl, cyclopentyl, cyclohexyl or cycloheptyl.

A group of preferred compounds of the invention is that in which $R_6$ is hydrogen, $R_7$ is a radical of formula (W) and Y is CH and Z is nitrogen or wherein $R_6$ is a radical of formula (W), $R_7$ is a hydrogen and Y is nitrogen and Z is CH. These compounds are represented by the formulae (1) and (2) respectively, wherein R, $R_1$, $R_2$, $R_3$, $R_4$, A, X, m, n, and p have the meanings defined for compounds of formula (I).

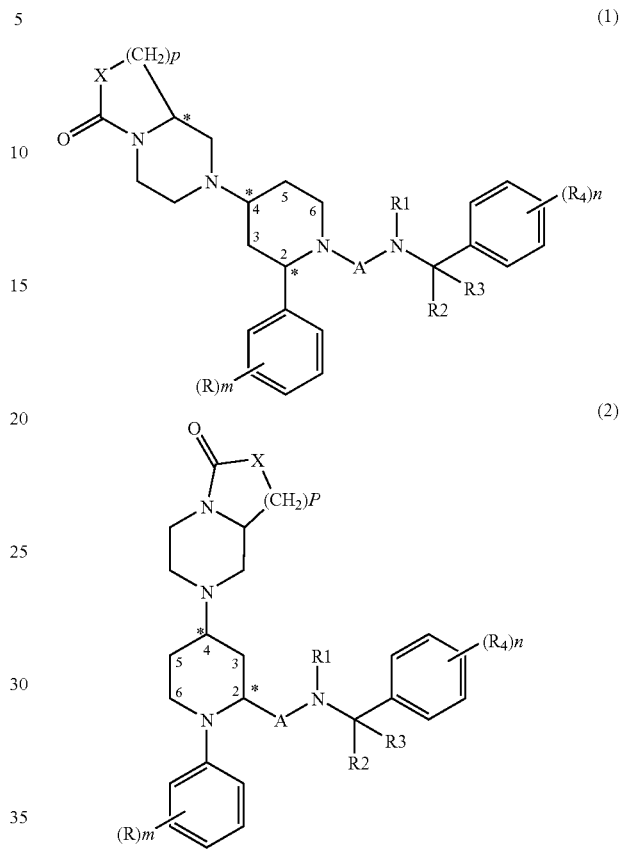

A preferred class of compounds of formula(I) is that wherein A is C(O).

Another preferred class of compounds of formula(I) is that wherein X is $CH_2$.

A further preferred class of compounds of formula(I) is that wherein p is 1.

When Y is CH and Z is Nitrogen, a preferred group of compounds of formula (I) is that in which the carbon atom at the 2-position of the piperidine ring is in the β configuration.

When Y is CH and Z is Nitrogen, a further preferred group of compounds of formula (I) is that in which the carbon atom at the 2-position of the piperidine ring and the carbon atom bearing the group (W) are in the β configuration.

A further preferred group of compounds of formula (I) is that in which the carbon atom at the 2-position of the piperidine ring and the carbon atom bearing the group (W) are in the syn configuration.

When R represents halogen, this is suitably chlorine or more preferably fluorine or when R is $C_{1-4}$ alkyl, this is suitably methyl or ethyl.

R is preferably a halogen (e.g. fluorine) and/or a $C_{1-4}$ alkyl (e.g. methyl) group and m is preferably zero or an integer from 1 to 2.

$R_1$ is preferably a methyl group.

$R_2$ is preferably a hydrogen atom or a methyl group.

$R_3$ is preferably a hydrogen atom or a methyl group.

$R_4$ is preferably a trifluoromethyl group or halogen (e.g. chlorine).

A preferred class of compounds of formula (I) is that wherein each R is independently a halogen (e.g. fluorine) or a $C_{1-4}$ alkyl (e.g. methyl) group, wherein m is 0, 1 or 2. More preferably, m is 1 or 2. Within this class, those wherein R is at the 2 and/or 4 position in the phenyl ring are particularly preferred.

Compounds of formula (I), wherein each $R_4$ is independently trifluoromethyl group or halogen (e.g. chlorine), n is 2, represent a preferred class of compounds and within this class the groups $R_4$ are preferably at the 3 and 5 position in the phenyl ring.

A group of preferred compounds of formula (I) is that wherein $R_6$ is hydrogen, $R_7$ is a radical of formula (W) and Y is CH and Z is nitrogen or wherein $R_6$ is a radical of formula (W), $R_7$ is a hydrogen and Y is nitrogen and Z is CH and A is C(O).

A group of further preferred compounds of formula (I) is that in which $R_6$ is hydrogen, $R_7$ is a radical of formula (W) and Y is CH and Z is nitrogen or wherein $R_6$ is a radical of formula (W), $R_7$ is a hydrogen and Y is nitrogen and Z is CH; A is C(O) and X is $CH_2$.

A group of further particularly preferred compounds of formula (1) is that in which $R_6$ is hydrogen, $R_7$ is a radical of formula (W) and Y is CH and Z is nitrogen or wherein $R_6$ is a radical of formula (W), $R_7$ is a hydrogen and Y is nitrogen and Z is CH;
A is C(O);
X is $CH_2$;
R is independently a halogen (e.g. fluorine) or a $C_{1-4}$ alkyl (e.g. methyl) group;
$R_4$ is a trifluoromethyl group;
m is 1 or 2;
n is 2;
p is 1.

Preferred compounds according to the invention are:
2-(R)-(4-Fluoro-2-methyl-phenyl)$_4$-(S)-(6-oxo-hexahydro-pyrrolo[1,2-a]-pyrazin-2-yl)-piperidine-1-carboxylic acid (3,5-bis-trifluoromethyl-benzyl)methylamide;
2-(R)-(4-Fluoro-2-methyl-phenyl)-4-(S)-(6-oxo-hexahydro-pyrrolo[1,2-a]-pyrazin-2-yl)-piperidine-1-carboxylic acid [1-(R)-(3,5-bis-trifluoromethyl-phenyl)ethyl]-methylamide;
1-(4-Fluoro-2-methyl-phenyl)-4-(6-oxo-hexahydro-pyrrolo[1,2-a]pyrazin-2-yl)-piperidine-2-carboxylic acid (3,5-bis-trifluoromethyl-benzyl)-methyl-amide;

and enantiomers, diastereoisomers pharmaceutically acceptable salts (e.g. hydrochloride, methanesulphonate or maleate) and solvates thereof.

Particular preferred compounds of the invention are:
2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide;
2-(R)-(4-Fluoro-2-methyl-phenyl)-4-(S)(8aR)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide;

and amorphous and crystalline forms thereof and pharmaceutically acceptable salts (e.g. hydrochloride or maleate) and solvates thereof.

Tachykinins are a family of peptides that share a common carboxyl-terminal sequence (PheX-Gly-Leu-Met-NH2). They are actively involved in the physiology of both lower and advanced lifeforms. In mammalian lifeforms, the main tachykinins are substance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1(SP-preferring), NK2 (NKA-preferring) and NK3 (NKB-preferring) which are widely distributed throughout the central nervous (CNS) and peripheral nervous system.

Particularly, the compounds of the invention are antagonists of the NK1 receptor.

By virtue of their efficacy as tachykinins receptor (expecially NK1 receptor) antagonists, the compounds of the present invention are particularly useful for the treatment of CNS disorders and psychotic disorders, in particular in the treatment or prevention of depressive states and/or in the treatment of anxiety.

$NK_1$-receptor binding affinity has been determined in vitro by measuring the compounds' ability to displace [3H]—substance P (SP) from recombinant human $NK_1$ receptor expressed in Chinese Hamster Ovary (CHO) cell membranes and from gerbil and marmoset brain cortex homogenates.

Membrane preparation from hNK1-CHO cells were performed essentially as described by Beattie et al. (Br. J. Pharmacol, 116: 3149–3157, 1995).

hNK1-CHO cells were harvested in phosphate buffered saline (PBS) containing 5 mM EDTA and centrifuged at 913 g for 8 min at 4° C. Cells were then re-suspended in 10 volumes of membrane-preparation buffer (HEPES 50 mM, pH 7.4, containing 0.1 mM leupeptin, 40 µg/ml bacitracin, 1 mM EDTA, 1 mM Pefabloc and 2 µM pepstatin A) and homogenised. The suspension was centrifuged at 48,000 g for 20 minutes at 4° C. The final pellet was resuspended in 10 volumes of membrane preparation buffer and re-homogenised. Suspensions of membrane were then frozen at −80° C. until required.

The assay volume of 200 µl consisted of 2 µl of DMSO or increasing concentrations of test compound dissolved in DMSO (1 pM–1 µM final concentration), 100 µl of [3H]-SP (0.5 nM final concentration), and 100 µl of membrane suspension (8 µg of protein per well) in incubation buffer (containing 50 mM HEPES, pH 7.4, 3 mM MnCl2, and 0.02% BSA). The incubation was carried out at room temperature for 40 min. Non-specific binding was defined by the addition of cold SP (1 µM). The reaction was stopped by rapid filtration. Filters were washed 5 times with 200 µl of ice-cold 0.9% w/v NaCl, and radioactivity was counted in a microplate scintillation counter. In each experiment, every concentration of displacer was tested in duplicate.

Mongolian gerbil (60 g, Charles River) and common marmoset (Callithrix jacchus, 300–400 g, GSK colony, Verona, Italy) brain cortex homogenates were prepared as follows: fresh tissues were weighed, crumbled and homogenised in 10 volumes of membrane-preparation buffer. The homogenate was then centrifuged at 48,000 g for 20 minutes, and the pellet was washed once more by resuspension in 10 volumes of membrane preparation buffer and centrifugation at 48,000 g for 20 minutes. The final pellet was re-suspended in 7–10 volumes of membrane preparation buffer and subdivided in aliquots frozen at −80° C. until use.

The assay volume of 400 µl consisted of 100 µl of incubation buffer (containing 50 mM HEPES, pH 7.4, 3 mM MnCl2, and 0.02% BSA), 4 µl of DMSO or increasing concentrations of test compound dissolved in DMSO (1 pM–1 µM final concentration), 100 µl of [3H]-SP (0.5 nM–0.8 nM final concentration) in incubation buffer and 200 µl of membrane suspension (0.6 mg protein for gerbil, and 0.8 mg protein for marmoset) in incubation buffer containing 2 µg/ml leupeptin, 20 µg/ml bacitracin and 0.5 µM phosphoramidon. The incubation proceeded at room temperature for 60 min. Non-specific binding was defined by the addition of cold SP (1 µM). The reaction was stopped by rapid filtration. Filters were washed 3 times with 1 ml ice cold wash buffer (containing 50 mM HEPES, pH 7.4, and 3 mM MnCl2), and radioactivity was counted in a liquid scintillation counter.

The potency of test compounds to inhibit SP or GR73632-induced increase of [Ca2+]i in hNK1/CHO cells was determined in functional experiments by using FLIPR (fluorimetric imaging plate reader) technology.

hNK1/CHO cells were seeded at a density of 60,000 cells per well and cultured overnight in Ham's F-12 medium supplemented with 10% (v/v) heat-inactivated foetal bovine serum and 2 mM glutamine. The cells were then incubated for the labelling in the culture medium containing the fluorescent calcium indicator Fluo-4 AM (2 µM), the organic anions transport blocker probenecid (5 mM), and HEPES (20 mM) for 30 min in a humidified atmosphere of 5% $CO_2$. After washing with Hanks' Balanced Salts Solution (HBSS) containing 20 mM HEPES and 2.5 mM probenecid, the cells were incubated for 60 min at 37C in wash buffer containing 0.02% BSA either in the absence (control) or in the presence of test compounds. The plates were then placed into a FLIPR to monitor cell fluorescence (ex=488 nm, em=510–570 nm) before and after the addition of different concentrations of SP or GR73632 in assay buffer. Experiments were carried out by using a laser setting of 1.0 W and a 0.4 sec charge coupled device (CCD) camera shutter speed.

Compounds of the invention have also been found to exhibit anxiolytic activity in conventional tests. For example in marmoset human threat test (Costall et al., 1988).

The action of the compounds of the invention at the $NK_1$ receptor may be determined by using conventional tests. Thus, the ability to penetrate the central nervous system and to bind at the $NK_1$ receptor was demonstrated in vivo by their inhibitory effect on the change in the behaviour induced by intracerebroventricular applied substance P in the gerbil, according to the gerbil foot tapping model as described by Rupniak & Williams, Eur. J. of Pharmacol., 265, 179–183, 1994.

Compounds of the invention are useful in the treatment of CNS disorders and psychotic disorders, in particular in the treatment or prevention of depressive states and/or in the treatment of anxiety as defined in, but not restricted to, Diagnostic Statistical of Mental Disorder (DSM) IV edition edit by American Psychiatric Association and International Classification Diseases 10th revision (ICD10).

Thus, for example, depressive states include Major Depressive Disorders (MDD), including bipolar depression, unipolar depression, single or recurrent major depressive episodes, recurrent brief depression, with or without psychotic features, catatonic features, melancholic features including anorexia, weight loss, atypical features, anxious depression, cyclothymic or postpartum onset.

Other mood disorders encompassed within the term major depressive disorders include dysthymic disorders with early or late onset and with or without atypical features, neurotic depression, post-traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

The term anxiety includes anxiety disorders, such as panic disorders with or without agoraphobia, agoraphobia, phobias, for example, social phobias or agoraphobia, obsessive-compulsive disorder, stress disorders including post-traumatic stress disorders, generalised anxiety disorders, acute stress disorders and mixed anxiety-depression disorders.

Compounds of the invention are useful as analgesics. In particular, they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondylitis; gout; burns; scar pain; itch and thalamic pain such as post stroke thalamic pain.

Compounds of the invention are also useful in the treatment of sleep disorders including dysomnia, insomnia, sleep apnea, narcolepsy, and circadian ritmic disorders.

Compounds of the invention are also useful in the treatment or prevention of the cognitive disorders. Cognitive disorders include dementia, amnestic disorders and cognitive disorders not otherwise specified.

Furthermore, compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds) or in the treatment of tolerance to and dependence on opiates (e.g. cannabis, heroin, morphine) or benzodiazepines; in the treatment of addiction to cocaine, sedative ipnotic, amphetamine or amphetamine-related drugs (e.g. dextroamphetamine, methylamphetamine) or a combination thereof.

Compounds of the invention are also useful as anti-inflammatory agents. In particular, they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal antiinflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia.

Compounds of the invention are also useful in the treatment of gastrointestinal disorders such as irritable bowel syndrome, gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia (such as ulcer-like dyspepsia, dysmotility-like dyspepsia and unspecified dyspepsia) chronic constipation; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The compounds of the invention are also useful in premenstrual dysphoric disorder (PMDD), in chronic fatigue syndrome and Multiple sclerosis.

Compounds of the invention have been found to exhibit anxiolytic and antidepressant activity in conventional tests. For example, in Guinea pig pups separation-induced vocalisations (Molewijk et al., 1996).

Compounds of the invention are also useful in the treatment of convulsions and epilepsy.

Compounds of the invention may be administered in combination with other active substances such as 5HT3 antagonists, serotonin agonists, selective serotonin reuptake inhibitors (SSRI), noradrenaline re-uptake inhibitors (SNRI), tricyclic antidepressants or dopaminergic antidepressants.

Suitable 5HT3 antagonists which may be used in combination with the compounds of the inventions include for example ondansetron, granisetron and metoclopramide.

Suitable serotonin agonists which may be used in combination with the compounds of the invention include sumatriptan, rauwolscine, yohimbine and metoclopramide.

Suitable SSRI which may be used in combination with the compounds of the invention include fluoxetine, citalopram, femoxetine, fluvoxamine, paroxetine, indalpine, sertraline and zimeldine.

Suitable SNRI which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and aminetpine.

It will be appreciated that the compounds of the combination may be administered simultaneously (either in the same or different pharmaceutical formulations) or sequentially.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In a further aspect of the invention there is provided the use of a compound of formula (I) or a pharmaceutically acceptable salt or solvate thereof in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus, compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g.

magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or nonaqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Compounds of formula (I), and salts and solvates thereof, may be prepared by the general methods outlined hereinafter. In the following description, the groups X, Y, Z, A, R. $R_1$, $R_2$, $R_3$, $R_4$, $R_5$, $R_6$, $R_7$, m, n and p, have the meaning as previously defined for compounds of formula (1) unless otherwise stated.

Compounds of formula (I) may be prepared by reductive N-alkylation of a compound of formula (II), wherein $R_8$ is =O and $R_9$ is hydrogen or $R_8$ is hydrogen and $R_9$ is =O

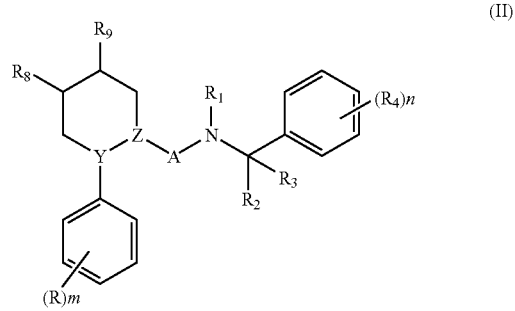

(II)

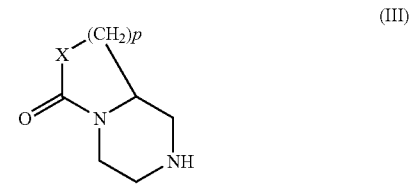

(III)

with diazabicycle derivatives (III) or salts thereof. The reaction is conveniently carried out in an aprotic solvent such as dichloroethane and in the presence of a suitable metal reducing agent such as sodium borohydride or sodium triacetoxyborohydride.

In a further embodiment of the invention, compounds of formula (I), wherein Y is CH, Z is nitrogen may be prepared by reaction of a compound of formula (IV)

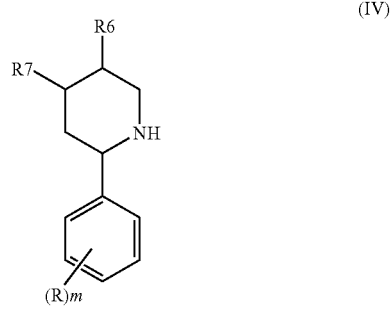

(IV)

-continued

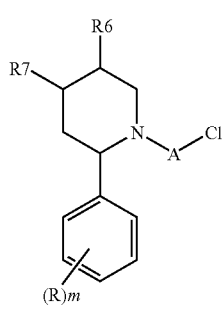

(V)

with triphosgene or S(O)pCl wherein p is an integer from 1 to 2 in an aprotic solvent such as dichloromethane and in the presence of an organic base such triethylamine to form the intermediate compound (V) in which A is C(O) or S(O)p respectively which may be isolated if required, followed by reaction of compound (V) with the amine compound (VI)

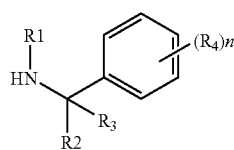

(VI)

The reaction conveniently takes place in an aprotic solvent such as a hydrocarbon, a halohydrocarbon such as dichloromethane or an ether such as tetrahydrofuran optionally in the presence of a base such as a tertiary amine e.g. diisopropylethylamine.

In a further embodiment of the invention, compounds of formula (I) wherein Y is nitrogen and Z is CH may be prepared by reaction of an activated derivative of the carboxylic acid of formula (VII), with amine (VI) or salts thereof, optionally in the presence of a suitable base.

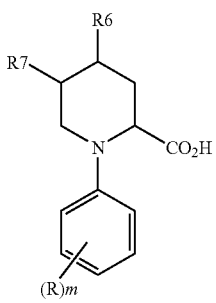

(VII)

Suitable activated derivatives of the carboxyl group include the corresponding acyl halide, mixed anhydride, activated ester such as a thioester or a derivative formed between the carboxylic acid group and a coupling agent such as that used in peptide chemistry, for example O-(benzotriazol-1-yl)-N,N,N'N'-tetramethyluronium tetrafluoroborate.

The reaction is preferably carried out in an aprotic solvent such as an ether, e.g. tetrahydrofuran, a halohydrocarbon, e.g. dichloromethane, N,N-dimethylformamide or acetonitrile.

Suitable base for use in this reaction include organic base such as triethylamine or N,N diisopropylethylamine.

The activated derivatives of the carboxylic acid (VII) may be prepared by conventional means. A particularly suitable activated derivative for use in this reaction is obtained by reaction of the carboxylic acid (II) with O-(benzotriazol-1-yl)-N,N,N'N'-tetramethyluronium tetrafluoroborate in a suitable aprotic solvent such as an ether e.g. tetrahydrofuran, a halohydrocarbon e.g. dichloromethane, an amide e.g. N,N-dimethylformamide or acetonitrile.

Compounds of formula (II), in which Y is CH, Z is nitrogen may be prepared by treating compounds of formula (VIII), wherein $R_8$ and $R_9$ have the meanings defined for compounds of formula (II) and Ra is a nitrogen protecting group,

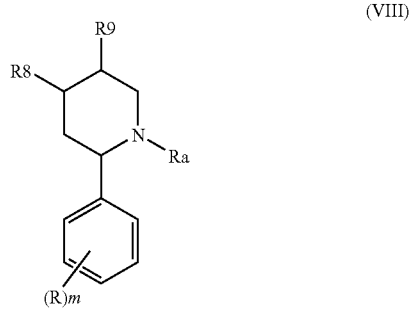

(VIII)

using, after removal of Ra, the same procedures described above for the preparation of compounds of formula (I) from compounds of formula (IV).

Compounds of formula (II), wherein $R_8$ and $R_9$ have the meanings defined for compounds of formula (II) and in which Y is nitrogen, Z is CH, may be prepared by treating compounds of formula (IX)

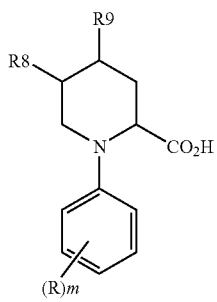

(IX)

using the same procedures described above for the preparation of compounds of formula (II) from compounds of formula (VII).

Compounds of formulae (IV) and (VII) may be prepared by reductive N-alkylation of a piperidine of formula (VIII) and a carboxylic acid (IX) or esters thereof (such as methyl, ethyl and the like) respectively with a diazabicycle derivatives (III) or salts thereof. The reaction is conveniently carried out in an aprotic solvent such as dichloroethane and in the presence of a suitable metal reducing agent such as sodium borohydride or sodium triacetoxyborohydride.

Examples of suitable nitrogen protecting groups Ra include alkoxycarbonyl e.g. t-butoxycarbonyl, benzyloxycarbonyl, arylsulphonyl e.g. phenysulphonyl or 2-trimethylsilylethoxymethyl.

Protection and deprotection may be effected using conventional techniques such as those described in "Protective Groups in Organic Synthesis $2^{nd}$ Ed." by T. W. Greene and P. G. M. Wuts (John Wiley and Sons, 1991) and as described in the examples hereinafter.

Compounds of formula (VIII) are either known compounds or may be prepared by analogous methods to those used for known compounds.

Thus, for example, compound (VIII) and enantiomers thereof may be prepared using Comins reaction as described in Journal American Chemical Society 1994, 116, 4719–4728, followed by reduction of 2,3 dihydro-1H-pyridin-4-one derivative to piperidine-4-one derivative. The reduction may be effected using hydrogen and metal catalyst e.g. palladium on a suitable support e.g. carbon or alumina. The reaction is carried out in a solvent such as ester e.g. ethyl acetate.

Compounds of formula (IX) wherein $R_8$ is =O and $R_9$ is hydrogen are known compounds and they may be prepared according to the procedures as described in Bioorganic & Medicinal Chemistry Letters, Vol 2, No. 11, pp 1357–1360, 1992.

Compounds of formula (IX) wherein $R_9$ is =O and $R_8$ is hydrogen are novel compounds and they may be prepared for example by reaction of an amine (XIV) with ethyl glyoxalate to obtain the intermediates (XIII) which may be converted into 4-oxo-tetrahydropyridine intermediates (XII) which in turn may be reduced to an intermediate of formula (XI). Said intermediate (XI) may be in turn hydrolysed, thus forming an intermediate of formula (IX).

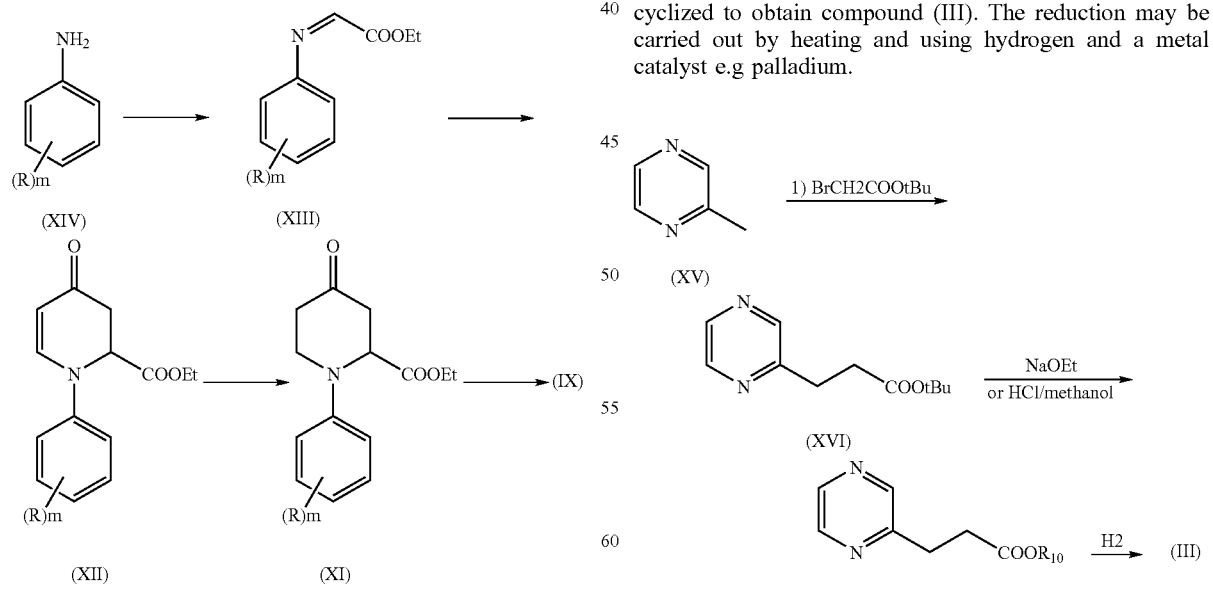

It will be appreciated by those skilled in the art that the compounds of formula (III) contain one chiral center (namely the carbon atom shown as* in the formulae IIIa and IIIb).

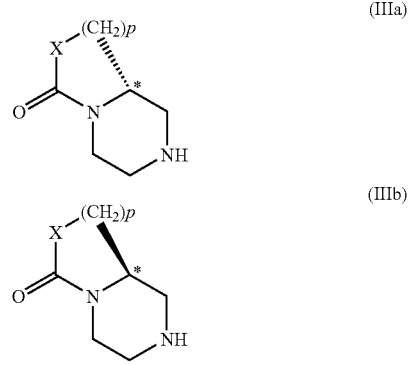

It is to be understood that the reference to compounds of formula (III) includes all stereoisomeric forms and all mixtures thereof.

Compounds of formula (III) are known compounds or may be prepared by analogous methods to those used for known compounds.

Thus, compounds of formula (III) wherein X is $CH_2$ and p is 1 may be prepared as described in Bioorganic & Medicinal Chemistry Letters, (1998) pages 3469–3474; or in Journal of Medicinal Chemistry, 2000 Vol 43 No. 10 pages 1969–1974.

Thus, in a particular embodiment of the invention, compounds of formula (III), wherein X is $CH_2$ and p is 1, may be prepared by reacting 2-methylpyrazine (XV) with a tert-butylhaloacetate such as for example tert-butylbromoacetate in the presence of a suitable base such as for example lithium diisopropylamine in an aprotic solvent such as tetrahydrofuran and at a temperature around −78° to obtain compound (XVI) which in turn may be converted into compound (XVII), wherein $R_{10}$ is methyl or ethyl, by reaction with sodium ethylate or with hydrochloride in methanol. Said compound may be subsequently reduced and cyclized to obtain compound (III). The reduction may be carried out by heating and using hydrogen and a metal catalyst e.g palladium.

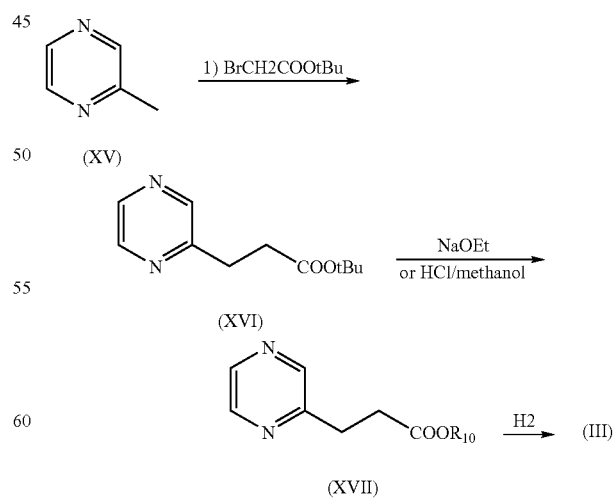

Where it is desired to isolate a compound formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compounds of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, for example, specific enantiomers of the compounds of formula (I) may be obtained from the corresponding enantiomeric mixture of a compound of formula (I) using chiral HPLC procedure.

Alternatively, enantiomers of a compound of general formula (I) may be synthesised from the appropriate optically active intermediates (III), (IV), (V),(VII), (VIII) and (IX) using any of the general processes described herein.

Thus, for example, the chiral compounds (III), (IV) and (VIII) may be prepared from the corresponding racemic compounds (III), (IV) and (VIII) using conventional procedures such as salt formation with a suitable optically active acid.

Suitable optically active acid for use in the process is L(+)mandelic acid or S)-(+)-O-acetylmandelic acid.

The chiral compounds (VII) and (IX) may be prepared from the corresponding racemic compounds (VII) and (IX) using conventional procedures such as salt formation with a suitable optically active amine.

Said diastereoisomeric salt forms are subsequently separated by conventional means e.g. chromatography and crystallisation and and the enantiomers are subsequently liberated by hydrolysis of the diastereoisomeric salts.

The invention is further illustrated by the following Intermediates and Examples which are not intended as a limitation of the invention.

In the Intermediates and Examples unless otherwise stated:

Melting points (m.p.) were determined on a Buchi m.p. apparatus and are uncorrected. R.T. or r.t. refer to room temperature.

Infrared spectra (JR) were measures in chloroform or nujol solutions on a FT-IR instrument. Proton Magnetic Resonance (NMR) spectra were recorded on Varian instruments at 400 or 500 MHz, chemical shifts are reported in ppm (δ) using the residual solvent line as internal standard. Splitting patterns are designed as s, singlet; d, double; t, triple; q, quartet; m, multiplet; b, broad. Mass spectra (MS) were taken on a VG Quattro mass spectrometer. Optical rotations were determined at 20° C. with a Jasco DIP360 instrument (1=10 cm, cell volume=1 mL,λ=589 nm). Flash silica gel chromatography was carried out over silica gel 230–400 mesh supplied by Merck AG Darmstadt, Germany. T.l.c. refers to thin layer chromatography on 0.25 mm silica gel plates (60F-254 Merck) and visualized with UV light Solutions were dried over anhydrous sodium sulphate.

Methylene chloride was redistilled over calcium hydride and tetrahydrofuran was redistilled over sodium.

The following abbreviation are used in the text: AcOEt=ethyl acetate, CH=cyclohexane, DCM=methylene chloride, DIPEA=N,N-diisopropylethylamine, DMF=N,N'-dimethylformamide, Et2O=diethyl ether, EtOH=ethanol, MeOH=methanol TEA=triethylamine, THF=tetrahydrofuran.

The X-ray powder diffraction pattern of a crystalline form of the compound of the invention was obtained by loading the sample into the diffractometer (Siemens D5005 X-ray diffractometer equipped with θ/θ goniometer, scintillation counter and graphite monochromator. The diffractometer was set up with the instrumental parameters given below.

Instrumental Parameters

MONOCHROMATIC RADIATION: Cu-1.54056/1.54439
2θRANGE: 2°–40° 2θ
GENERATOR VOLTAGE/CURRENT: 40 kV/50 mA
STEP SIZE: 0.04° 2θ
TIME PER STEP: 2 sec$^{-1}$
ROTATION: off
DIVERGENCE/ANTISCATTERING SLIT: variable (fixed area)
SAMPLE HOLDER: TTK sample holder (Alan Paar instruments)
TEMPERATURE: 25° C.

The spectrum obtained was analysed using the data evaluation software EVA3.0.

Intermediate 1

1-(Benzyloxycarbonyl)-2-(4-fluoro-2-methyl-phenyl)-2,3-dihydro-4-pyridone

A small amount of iodine was added to a suspension of magnesium turnings (13.2 g) in dry THF (300 mL), at r.t., under a nitrogen atmosphere, then the mixture was vigorously refluxed for 20 minutes. To this suspension, a 15% of a solution of 2-bromo-5-fluoro-toluene (52.5 mL) in anhydrous THF (300 mL) was added. The suspension was heated under vigorous reflux until the brown colour disappeared. The remaining part of the bromide solution was added drop-wise over 1 hour to the refluxing suspension which was then stirred for a further 1 hour. This solution of Grignard reagent was then added drop-wise to the pyridinium salt obtained from benzyl chloroformate (48.7 mL) and 4-methoxypyridine (25 mL) in dry THF (900 mL) at −2° C.

The obtained solution was stirred 1 hour at −20° C. then it was warmed up to 20° C., a 10% hydrochloric acid solution (560 mL) was added and the aqueous layer was extracted with AcOEt (2×750 mL).

The combined organic extracts were washed with 5% sodium hydrogen carbonate solution (600 mL) and brine (600 mL) then partially concentrated in vacuo.

CH (400 mL) was added drop-wise over 1 hour at 20° C. and the resulting mixture was stirred 30 minutes and then filtered to give the title compound as a white solid (66 g).

IR (nujol, cm$^{-1}$): 1726 and 1655 (C═P), 1608 (C═C). NMR (d$_6$-DMSO): δ (ppm) 8.19 (d, 1H); 7.31–7.18 (m, 5H); 7.08 (m, 2H); 6.94 (dt, 1H); 5.77 (d, 1H); 5.36 (d, 1H); 5.16 (2d, 2H); 3.26 (dd, 1H); 2.32 (d, 1H); 2.26 (s, 3H). MS (ES/+): m/z=340 [MH]$^+$.

Intermediate 2

2-(4-Fluoro-2-methyl-phenyl)-piperidine-4-one

Method A:

4-Fluoro-2-methyl-benzaldehyde (4 g) was added to a solution of 4-aminobutan-2-one ethylene acetal (3.8 g) in dry benzene (50 mL) and the solution was stirred at r.t. under a nitrogen atmosphere. After 1 hour the mixture was heated at reflux for 16 hours and then allowed to cool to r.t. This solution was slowly added to a refluxing solution of p-toluenesulphonic acid (10.6 g) in dry benzene (50 mL) previously refluxed for 1 hour with a Dean-Stark apparatus. After 3.5 hours the crude solution was cooled and made basic with a saturated potassium carbonate solution and taken up with AcOEt (50 mL). The aqueous phase was extracted with AcOEt (3×50 mL) and Et2O (2×50 mL). The organic layer was dried and concentrated in vacuo to a yellow thick oil as residue (7.23 g). A portion of the crude mixture (3 g) was dissolved in a 6N hydrochloric acid solution (20 mL) and stirred at 60° C. for 16 hours. The solution was basified with solid potassium carbonate and extracted with DCM (5×50 mL). The combined organic phases were washed with brine (50 mL), dried and concentrated in vacuo to give the title compound (2.5 g) as a thick yellow oil.

Method B

L-selectride (1M solution in dry THF, 210 mL) was added drop-wise, over 80 minutes, to a solution of intermediate 1 (50 g) in dry THF (1065 mL) previously cooled to −72° C. under a nitrogen atmosphere. After 45 minutes, 2% sodium hydrogen carbonate solution (994 mL) was added drop-wise and the solution was extracted with AcOEt (3×994 mL). The combined organic phases were washed with water (284 mL) and brine (568 mL). The organic phase was dried and concentrated in vacuo to get 1-benzyloxycarbonyl-2-(4-fluoro-2-methylphenyl)-piperidine-4-one as a pale yellow thick oil (94 g) which was used as a crude.

This material (94 g) was dissolved in AcOEt (710 mL), then 10% Pd/C (30.5 g) was added under a nitrogen atmosphere. The slurry was hydrogenated at 1 atmosphere for 30 minutes. The mixture was filtered through Celite and the organic phase was concentrated in vacuo to give the crude 2-(4-fluoro-2-methyl-phenyl)-piperidine-4-one as a yellow oil. This material was dissolved in AcOEt (518 mL) at r.t. and racemic camphorsulphonic acid (48.3 g) was added. The mixture was stirred at r.t for 18 hours, then the solid was filtered off, washed with AcOEt (2×50 mL) and dried in vacuo for 18 hours to give 2-(4-fluoro-2-methyl-phenyl)-piperidine-4-one, 10-camphorsulfonic acid salt as a pale yellow solid (68.5 g). (M.p.: 167–169° C. —NMR (d$_6$-DMSO): δ (ppm) 9.43 (bs, 1H); 9.23 (bs, 1H); 7.66 (dd, 1H); 7.19 (m, 2H); 4.97 (bd, 1H); 3.6 (m, 2H); 2.87 (m, 3H); 2.66 (m, 1H); 2.53 (m, 2H); 2.37 (s+d, 4H); 2.22 (m, 1H); 1.93 (t, 1H); 1.8 (m, 2H); 1.26 (m, 2H); 1.03 (s, 3H); 0.73 (s, 3H).

This material (68.5 g) was suspended in AcOEt (480 mL) and stirred with a saturated sodium hydrogen carbonate (274 mL). The organic layer was separated and washed with further water (274 mL). The organic phase was dried and concentrated in vacuo to give the title compound (31 g) as a yellow-orange oil.

NMR (d$_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H). MS (ES/+): m/z=208 [MH]$^+$.

Intermediate 3

2-(4-Fluoro-2-methyl-phenyl)-4-oxo-piperidine-1-carboxylic acid (3,5-bis-trifluoromethyl-benzyl)-methylamide A solution of triphosgene (1.43 g) dissolved in dry DCM (10 mL) was added to a solution of intermediate 2 (2.5 g) and DIPEA (8.4 mL) in dry DCM (20 mL) previously cooled to 0° C. under a nitrogen atmosphere. The solution was stirred at 0° C. for 2 hours, then (3,5-bis-trifluoromethyl-benzyl)methylamine hydrochloride (5.63 g) and DIPEA (3.34 mL) were added. The mixture was stirred under nitrogen at r. t. for 14 hours. The mixture was taken up with AcOEt (50 mL), washed with cold 1N hydrochloric acid solution (3×20 mL) and brine (10 mL). The organic layer was dried and concentrated in vacuo to a residue which was purified by flash chromatography (AcOEt/CH 3:7) to give the title compound as a white foam (3.85 g).

IR (nujol, cm$^{-1}$): 1721 and 1641 (C=O). NMR (d$_6$-DMSO): δ (ppm) 7.96 (s, 11; 7.76 (s, 2H); 7.25 (dd, 1 H); 6.97 (dd, 1H); 6.90 (dt, 1H); 5.22 (t, 1H); 4.59 (d, 1H); 4.43 (d, 1H); 3.63–3.49 (m, 2H); 2.79 (s, 3H); 2.69 (m, 2H); 2.49 (m, 2H); 2.26 (s, 3H).

MS (ES/+): m/z=491 [MH]$^+$.

Intermediate 4

2-(R)-(4-Fluoro-2-methyl-phenyl)-4-oxo-piperidine-1-carboxylic acid [1-(R)-3,5-bis-trifluoromethyl-phenyl)-ethyl]-methylamide (4a) and 2-(S)-(4-Fluoro-2-methyl-phenyl)-4-oxo-piperidine-1-carboxylic acid [1-(R)-3,5-bis-trifluoromethyl-phenyl)ethyl]-methylamide (4b)

Method A:

A solution of triphosgene (147 mg) dissolved in dry DCM (5 mL) was added drop-wise to a solution of intermediate 2 (250 mg) and DIPEA (860 μL) in dry DCM (15 mL) previously cooled to 0° C. under a nitrogen atmosphere. After 2 hours, [1-(R)-3,5-bis-trifluoromethylphenyl)-ethyl]-methylamine hydrochloride (503 mg) and DIPEA (320 μL) in dry acetonitrile (20 mL) were added and the mixture was heated to 70° C. for 16 hours. Further [1-(R)-(3,5-bis-trifluoromethyl-phenyl)-ethyl]-methylamine hydrochloride (170 mg) and DIPEA (100 μL) were added and the mixture was stirred at 70° C. for further 4 hours. Next, the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 4a (230 mg) as a white foam,
2. intermediate 4b (231 mg) as a white foam.

Intermediate 4a

NMR (d$_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

Intermediate 4b

NMR (d$_6$-DMSO): δ (ppm) 7.96 (bs, 1H); 7.75 (bs, 2H); 7.24 (dd, 1H); 6.98 (dd, 1H); 6.93 (dt, 1H); 5.29 (q, 1H); 5.24 (t, 1H); 3.56 (m, 1H); 3.48 (m, 1H); 2.70 (s, 3H); 2.50 (m, 4H); 2.26 (s, 3H); 1.54 (d, 3H).

Intermediate 4a

Method B

A saturated sodium hydrogen carbonate solution (324 mL) was added to a solution of intermediate 9 (21.6 g) in AcOEt (324 mL) and the resulting mixture was vigorously stirred for 15 minutes. The aqueous layer was back-extracted with further AcOEt (216 mL) and the combined organic extracts were dried and concentrated in vacuo to give intermediate 8 as a yellow oil, which was treated with TEA (19 mL) and AcOEt (114 mL). The solution obtained was added drop-wise over 40 minutes to a solution of triphosgene (8 g) in AcOEt (64 mL) previously cooled to 0° C. under a nitrogen atmosphere, maintaining the temperature between 0° C. and 8° C. After stirring for 1 hours at 0° C. and for 3 hours at 20° C., [1 (R)-(3,5-bis-trifluoromethylphenyl)-ethyl]-methylamine hydrochloride (29.7 g), AcOEt (190 mL) and TEA (38 mL)were added to the reaction mixture which was then heated to reflux for 16 hours.

The solution was washed with 10% sodium hydroxide solution (180 mL), 1% hydrochloric acid solution (4×150 mL), water (3×180 mL) and brine (180 mL). The organic layer was dried and concentrated in vacuo to a residue, which was purified through a silica pad (CH/AcOEt 9:1) to give the title compound (21.5 g) as a brown thick oil.

NMR (d$_6$-DMSO): δ (ppm) 7.97–7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

Intermediate 5

2-(S)-(4-Fluoro-2-methyl-phenyl)-4-oxo-piperidine-1-carboxylic acid [1-(S)-(3,5-bis-trifluoromethyl-phenyl)ethyl]-methylamide (5a) and 2-(R)-(4-Fluoro-2-methyl-phenyl)-4-oxo-piperidine-1-carboxylic acid [1-(S)-(3,5-bis-trifluoromethyl-phenyl)ethyl]-methylamide (5b)

A solution of triphosgene (147 mg) dissolved in dry DCM (5 mL) was added to a solution of intermediate 2 (250 mg) and DIPEA (860 μL) in dry DCM (15 mL) previously cooled to 0° C. under a nitrogen atmosphere. After 2 hours, a solution of [1-(S)-(3,5-bis-trifluoromethylphenyl)-ethyl]-methylamine hydrochloride (510 mg) and DIPEA (320 μL) in dry acetonitrile (20 mL) was added and the mixture was heated to 70° C. for 16 hours. Next, further [1-(S)-(3,5-bis-trifluoromethyl-phenyl)-ethyl]-methylamine hydrochloride (170 mg) and DIPEA (105 μL) were added. After further 4 hours at 70° C., the mixture was allowed to cool to r.t., taken up with AcOEt (30 mL), washed with a 1N hydrochloric acid cold solution (3×15 mL) and brine (2×10 mL). The organic layer was dried and concentrated in vacua to a residue, which was purified by flash chromatography (CH/AcOEt 8:2) to give:
1. intermediate 5a (234 mg) as a white foam,
2. intermediate 5b (244 mg) as a white foam.

Intermediate 5a

NMR (d$_6$-DMSO): δ (ppm) 7.97–7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

Intermediate 5b

NMR (d$_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

Intermediates 6

2-(S)-(4-Fluoro-2-methyl-phenyl)-4-oxo-3,4-dihydro-2H-pyridine-1-carboxylic acid (1R, 2S, 5R)-2-isopropyl-5-methyl-cyclohexyl ester (6a) and 2-(R)(4-Fluoro-2-methyl-phenyl)-4-oxo-3,4-dihydro-2H-pyridine-1-carboxylic acid (1R, 2S, 5R)-2-isopropyl-5-methyl-cyclohexyl ester (6b)

A solution of 2-bromo-5-fluoro-toluene (3.68 g) in dry THF (10 mL) was dropped over 30 minutes, into a mixture of magnesium (525 mg) and iodine (1 crystal) in dry THF (5 mL) previously heated to 70° C. under a nitrogen atmosphere. The mixture was stirred at 70° C. for 1.5 hours, then allowed to cool to r.t.

A solution of (−)-mentyl chloroformate (3.53 mL) in dry THF (15 mL) was added to a solution of 4-methoxypyridine (1.52 mL) in dry THF (35 mL) previously cooled to −78° C. under a nitrogen atmosphere. After 15 minutes, the solution containing the 4-fluoro-2-methyl-phenyl magnesium bromide was added drop-wise, and the mixture was stirred at −78° C. for 1 hour. The reaction was quenched by the addition of 1M hydrochloric acid solution (20 mL), warmed to r.t. and stirred at 23° C. for 30 minutes. After extraction with AcOEt (2×150 mL), the combined organic extracts were washed with brine (50 mL), dried and concentrated in vacuo to a residue, which was purified by flash chromatography (CH/THF/toluene 8:1:1) to give:
1. intermediate 6a (3.44 g—yellow oil)
2. intermediate 6b (530 mg—white solid).

Intermediate 6a

T.l.c.: CH/THF/toluene 7:2:1, Rf=0.59.

IR (nujol, cm$^{-1}$): 1718 and 1675 (C=O). NMR (d$_6$-DMSO): δ (ppm) 8.14 (d, 1H); 7.08 (dd, 1H); 7.02 (dd, 1H); 6.95 (m, 1H); 5.68 (d, 1H); 5.34 (d, 1H); 4.47 (m, 1H); 3.26 (dd, 1H); 2.30 (m, 4H); 1.7 (m, 4H); 1.33 (m, 2H); 0.8 (m, 11H).

Intermediate 6b

M.p.: 117–120° C. T.l.c.: CH/THF/toluene 7:2:1, Rf=0.56.IR (nujol, cm$^{-1}$): 1718 and 1669 (C=O). NMR (d$_6$-DMSO): δ (ppm) 8.17 (d, 1H); 7.04–6.94 (m, 3H); 5.70 (d, 1H); 5.35 (d, 1H); 4.42 (m, 1); 3.26 (dd, 1H); 2.30 (m, 4H); 1.58–1.40 (m, 3H); 1.2–0.7 (m, 8H); 0.51–0.34 (bs, 6H):

Intermediate 7

2-(R)-(4-Fluoro-2-methyl-phenyl)-2,3-dihydro-1H-pyridin-4-one

Sodium methoxide (100 mg) was added to a solution of intermediate 6b (170 mg) in MeOH (15 mL) under a nitrogen atmosphere. The mixture was refluxed for two hours and the solvent was removed in vacuo. The residue was partitioned between water (10 mL) and AcOEt (15 mL). The layers were separated, and the aqueous phase was extracted with further AcOEt (4×10 mL). The combined organic extracts were washed with brine (10 mL), dried and concentrated in vacuo to give the title compound (145 mg) as a light yellow oil.

NMR (d$_6$-DMSO): δ (ppm) 7.71 (bd, 1H); 7.45 (dd, 1H); 7.38 (t, 1H); 7.03 (m, 2H); 4.86 (dd, 1H); 4.77 (d, 1H); 2.42 (dd, 1H); 2.31 (m, 4H). MS (ES/+): m/z=206 [M+H]$^+$.

Intermediate 8

2-(R)-(4-Fluoro-2-methyl-phenyl)-piperidin-4-one

Palladium over charcoal (10%-74 mg) was added to a solution of intermediate 7 (145 mg) in MeOH (8 mL) and THF (2 mL). The mixture was allowed to react with hydrogen in a pressure reactor (2 atm) overnight. After flushing with nitrogen, the solution was filtered and the solvent removed in vacuo. The crude product was purified by flash chromatography (AcOEt/MeOH 9:1) to give the title compound (26 mg) as a yellow oil.

The enantiomeric excess (90–95%) was detected by chiral HPLC.

T.l.c.:AcOEt/MeOH 9:1, Rf=0.2.

NMR (d$_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H). MS (ES/+): m/z=208 [MH]$^+$. [λ]$_D$=+82.1 (c=1.07, DMSO).

Intermediate 9

2-(R)-(4-Fluoro-2-methyl-phenyl)-piperidin-4-one L-(+)-mandelate

A solution of L-(+)-mandelic acid (22.6 g) in AcOEt (308 mL) was added to a solution of intermediate 2 (31 g) in AcOEt (308 mL). Then isopropanol (616 mL) was added and the solution was concentrated in vacuo to 274 mL. The solution was then cooled to 0° C. and further cold isopropanol (96 mL) was added. The thick precipitate was stirred under nitrogen for 5 hours at 0° C., then filtered and washed with cold Et2O (250 mL) to give the title compound as a pale yellow solid (20.3 g).

M.p.: 82–85° C. NMR (d$_6$-DMSO): δ (ppm) 7.51 (dd, 1H); 7.40 (m, 2H); 7.32 (m, 2H); 7.26 (m, 1H); 7.0 (m, 2H); 4.95 (s, 1H); 4.04 (dd, 1H); 3.31 (m, 1H); 2.88 (m, 1H); 2.49–2.2 (m, 4H); 2.29 (s, 3H). Chiral HPLC: HP 1100 HPLC system; column Chiralcel OD-H, 25 cm×4.6 mm; mobile phase: n-hexane/isopropanol 95:5+1% diethylamine; flow: 1.3 ml/min; detection: 240/215 nm; retention time 12.07 minutes.

Intermediate 10

2-(R)-4-Fluoro-2-methyl-phenyl)-4-oxo-piperidine-1-carboxylic acid (3,5-bis-trifluoromethyl-benzyl)methylamide Method A A solution of triphosgene (17 mg) in dry DCM (2 mL) was added to a solution of intermediate 8 (26 mg) and DIPEA (65 mg) in dry DCM (3 mL) previously cooled to 0° C. under a nitrogen atmosphere. After two hours acetonitrile (10 mL) was added, the temperature was allowed to reach r.t. and the DCM evaporated under a nitrogen flush. Then, a solution of 3,5-(bis-trifluoromethyl-benzyl)-methylamine hydrochloride (74 mg) and DIPEA (130 mg) in acetonitrile (3 mL) was added and the mixture was stirred at 23° C. overnight. The solvent was concentrated in vacuo. The residue was dissolved in AcOEt (10 mL) and washed with 1N hydrochloric acid solution (3×5 mL), 5% sodium hydrogen carbonate (5 mL) and brine (10 mL). The organic layer was dried and concentrated in vacuo to a residue, which was purified by flash chromatography (CH/AcOEt 1:1) to give the title compound (50 mg) as a white solid.

Method B

A saturated sodium hydrogen carbonate solution (348 mL) was added to a solution of intermediate 9 (23.2 g) in AcOEt (348 mL) and the resulting mixture was vigorously stirred for 15 minutes. The aqueous layer was back-extracted with further AcOEt (230 mL) and the combined organic extracts were dried and concentrated in vacuo to give intermediate 8 (12.31 g) as a yellow oil, which was treated with TEA (20.5 mL) and AcOEt (123 mL). The solution obtained was added drop-wise over 40 minutes to a solution of triphosgene (8 g) in AcOEt (61 mL) previously cooled to 0° C. under a nitrogen atmosphere, maintaining the temperature between 0° C. and 8° C.

After stirring for 2 hours at 20° C., 3,5-(bis-trifluoromethyl-benzyl)-methylamine hydrochloride (28.1 g), AcOEt (184 mL) and TEA (33 mL) were added to the reaction mixture which was then further stirred for 2 hours at 20° C.

The solution was washed with 10% sodium hydroxide solution (3×185 mL) and 1% hydrochloric acid solution (3×185 mL). The organic layer was dried and concentrated in vacuo to a crude (38 g), which was purified through a silica pad (CH/AcOEt from 9:1 to 1:1) to give the title compound (24.7 g) as a colourless oil.

NMR (d$_6$-DMSO): δ (ppm) 7.96 (s, 1H); 7.76 (s, 2H); 7.26 (dd, 1H); 6.98 (dd, 1H); 6.90 (td, 1H); 5.23 (t, 1H); 4.61 (d, 1H); 4.41 (d, 1H); 3.60 (m, 2H); 2.69 (m, 2H); 2.79 (s, 3H); 2.50 (m, 2H); 2.27 (s, 3H). MS (ES/+): m/z=491 [MH]$^+$.

Intermediate 11

1,4-Dibenzyl-2-piperazinecarboxaldehyde

A solution of ethyl 2,3-dibromopropionate (6 mL) in anhydrous toluene (50 mL) was added to a solution of N,N'-dibenzylethylenediamine (5 g) and DIPEA (12 mL) in anhydrous toluene (50 mL) under a Nitrogen atmosphere. The resulting mixture was heated to 100° C. for 21 hours, then allowed to cool to r.t., diluted with AcOEt (100 mL) and washed with brine (3×100 mL). The organic extract was dried and concentrated in vacua to a residue which was purified by flash chromatography (CH/AcOEt 9:1) to give ethyl 1,4-dibenzyl-piperazine-2-carboxylate (5.65 g) as a yellow oil, which was used without any purification in the next step. Diisobutylaluminium hydride (1M in toluene—29 mL) was dropped into a solution of ethyl 1,4-dibenzyl-piperazine-2-carboxylate (5.47 g) in anhydrous toluene (110 mL) previously cooled to −78° C. under a Nitrogen atmosphere. The solution was stirred at −78° C. for 1 hour, then a 20% sodium hydroxide solution (20 mL) was added and the mixture was allowed to warm to r.t. Further 20% sodium hydroxide solution (50 mL) was added and the solution was extracted with Et2O (2×150 mL). The combined organic extracts were dried and concentrated in vacuo to give the title compound (5.33 g) as a crude, which was used without any further purification in the next step.

T.l.c.: CH/AcOEt 8:2, Rf=0.36. NMR (d$_6$-DMSO): δ (ppm) 9.62 (s, 1H); 7.4–7.15 (m, 10H); 3.86 (d, 1H); 3.6 (d, 1H); 3.46 (s, 2H); 3.09 (bt, 1H); 2.82 (t, 1H); 2.55–2.45 (m, 2H); 2.4–2.3 (m, 3H).

Intermediate 12

Hexahydro-pyrrolo[1,2-a]pyrazin-6-one

Method A:

(Carbethoxymethylene)triphenylphosphorane (11.72 g) was added in two portions to a solution of intermediate 11 (4.95 g) in anhydrous toluene (100 mL) under a Nitrogen atmosphere. The mixture was heated to 80° C. for 24 hours, then it was allowed to cool to r.t. and washed with water (100 mL). The organic layer was dried and concentrated in vacua to a residue, which was purified by flash chromatography (CH/AcOEt 85:15) to give ethyl 1,4-dibenzyl-2-piperazine-3-acrylate (4.2 g—T.l.c.: CH/AcOEt 8:2, Rf=0.36).

A solution of ethyl 1,4-dibenzyl-2-piperazine-3-acrylate (2.84 g) in abs. EtOH (40 mL) was hydrogenated over Pd/C 10% (1.42 g) at 3.5 atm. for 2 days. After filtration, the solution was concentrated to nearly 30 mL and heated to 70° C. for 16 hours until complete cyclization occurred. The solution was concentrated in vacuo and the residue was purified by flash chromatography (DCM/MeOH 7:3) to give the title compound (820 mg) as a pale yellow oil.

Method B:

Diisobutylaluminium hydride (1.2M in toluene—262 mL) was dropped into a solution of ethyl 1,4-dibenzyl-piperazine-2-carboxylate (48.4 g) synthesised as previously described in anhydrous toluene (450 mL) previously cooled to −78° C. under a Nitrogen atmosphere (addition of DIBAL-H took 1.5 hours and the internal temperature was always maintained below −70° C.). The solution was stirred at −78° C. for 2 hour, then a 10% sodium hydroxide solution (500 mL) was added and the mixture was allowed to warm to r.t. Further 10% sodium hydroxide solution (400 mL) was added and the solution was extracted with toluene (2×250 mL). The combined organic extracts were dried and concentrated in vacuo until a volume of 100 mL containing 1,4-dibenzyl-2-piperazinecarboxaldehyde, which was used without any further purification in the next step.

(Carbethoxymethylene)triphenylphosphorane (75 g) was added in two portions to the previous solution of 1,4-dibenzyl-2-piperazine carboxaldehyde in toluene (450 mL) under a Nitrogen atmosphere. The mixture was heated to 80° C. overnight, then it was allowed to cool to r.t. and washed with water (2×400 mL) and brine (250 mL) The organic layer was dried and concentrated in vacuo to a residue, which was purified by flash chromatography (CH/AcOEt 85:15) to give ethyl 1,4-dibenzyl-2-piperazine-3-acrylate (44.8 g—T.l.c.: CH/AcOEt 8:2, Rf=0.36).

To a solution of ethyl 1,4-dibenzyl-2-piperazine-3-acrylate (44.8 g) in MeOH (450 mL) under a Nitrogen atmosphere, ammonium formate (23.2 g) and 5% palladium on charcoal (8.96 g) were added. The resulting mixture was heated to reflux temperature for 6 h. After filtration over Celite, the solution was concentrated in vacuo and the residue was purified by flash chromatography (DCM/MeOH 8:2) to give the title compound (14.15 g) as a pale yellow oil.

Method C:

Intermediate 15 (820 g) and toluene (1680 g) were charged in a 5 L stainless steel autoclave and palladium on charcoal (5%, dry—50 g) was added. The autoclave was rendered inert with nitrogen, subsequently filled with 100 bar hydrogen, and then heated to 100° C. When the internal pressure has fallen to 90 bar, the pressure was increased to 100 bar again. After the hydrogen uptake ceased, the autoclave was cooled below 30° C. and the reaction solution was removed. The catalyst was then filtered off with a buchner funnel and washed with toluene (2×200 mL). After concentrating the filtrate with a rotatory evaporator, the product was distilled over a 15 cm Vigreux column (bp: 115 to 125° C. @ 0.07 mbar) giving title compound 12 (574 g) as a slightly yellowish oil.

T.l.c.: DCM/MeOH 7:3, Rf=0.17 (detection with ninhydrin) NMR (CDCl3): δ (ppm) 4.01(m, 1H); 3.54 (m, 1H); 3.16 (m, 1H); 3.01 (m, 1H); 2.81 (m, 1H); 2.6 (dt, 1H); 2.38 (m, 3H); 2.16 (m, 1H); 1.6 (m, 1H). MS (ES/+): m/z=141 [M+H]$^+$ Intermediates 13

(8aS)-Hexahydro-pyrrolo[1,2-a]pyrazin-6-one (13a) and (8aR)-Hexahydro-pyrrolo[1,2-a]pyrazin-6-one (13b)

Method A:

Intermediate 12 (746 mg) was separated into the enantiomers via preparative HPLC (Column: Chiralpack AD 25×2 cm; mobile phase: n-hexane/EtOH 8:2; flux=1 mL/min; λ=225 nm). Thus, intermediate 13a (330 mg) and intermediate 13b (320 mg) were obtained.

Intermediate 13a (enantiomer 1):

HPLC: Column Chiralpack AD 25 cm×4.6 mm×5μ; mobile phase n-hexane/EtOH 8:2; flux=1 mL/min; λ=225 nm; retention time 10.7 minutes. Ratio 13a/13b=100:0.

Intermediate 13b (enantiomer 2):

HPLC: Column Chiralpack AD 25 cm×4.6 mm×5μ; mobile phase n-hexane/EtOH 8:2; flux=1 mL/min; λ=225 nm; retention time 12.8 minutes. Ratio 13a/13b=0:100.

Intermediate 13b:

Method B:

A solution of L-(+)-mandelic acid (13.03 g) in isopropanol (60 mL) was dropped over 20 minutes into a solution of intermediate 12 (12 g) in isopropanol (60 mL) under a Nitrogen atmosphere. The suspension was stirred at 23° C. for 2 hours, then it was filtered off and washed with further isopropanol (120 mL). The solid obtained (ratio enantiomers 20:80) was recrystallized three times from isopropanol (10 volumes) until a complete HPLC enantioselectivity was detected. In this way, (8aR)-hexahydro-pyrrolo[1,2-a]pyrazin-6-one L-(+)-mandelate (5.84 g—enantiomer 2) was obtained.

This material (6.469 g) was dissolved in EtOH (40 mL) and water (4 mL) and stirred with a suspension of resin IRA68 (112 g—previously washed with a 0.05N sodium hydroxide solution (370 mL) and water (4 L) until neutral pH) in EtOH (200 mL). The mixture was stirred at 23° C. for 1.5 hours, then filtered off. The organic layer was concentrated in vacuo to give the title compound 13b (3.1 g) as a white solid.

Intermediate 13b:

HPLC: Column Chiralpack AD 25 cm×4.6 mm×5μ; mobile phase n-hexane/EtOH 8:2; flux=1 mL/min; λ=225 nm; retention time 12.8 minutes. Ratio 13a/13b=0:100.

Intermediate 13a:

Method B:

A part of the mother liquors (3.48 g with ratio 13a:13b=63:37) was treated with a suspension of resin IRA68 (70 g—previously washed with a 0.05N sodium hydroxide solution (150 mL) and water until neutral pH) in EtOH (150 mL) and water (1 mL). The mixture was stirred at 23° C. for 2 hours, then filtered off. The organic layer was concentrated in vacuo to give the free hexahydro-pyrrolo[1,2-a]pyrazin-6-one (1.6 g) as colourless oil. This material (1.6 g) was dissolved in isopropanol (8 mL) and treated with a solution of D-(−)-mandelic acid (1.74 g) in isopropanol (8 mL).

The suspension was stirred at 23° C. for 16 hours, then it was filtered off and washed with further isopropanol (120 mL). The solid obtained (ratio enantiomers 86:14) was recrystallized three times from isopropanol (10 volumes) until a complete HPLC enantioselectivity was detected. In this way, (8aS)-hexahydro-pyrrolo[1,2-a]pyrazin-6-one D-(−)-mandelate (0.88 g—enantiomer 1) was obtained.

This material (0.88 g) was dissolved in EtOH (10 mL) and water (1 mL) and stirred with a suspension of resin IRA68 (15 g—previously washed with a 0.05N sodium hydroxide solution (50 mL) and water until neutral pH in EtOH (30 mL). The mixture was stirred at 23° C. for 1 hour, then filtered off. The organic layer was concentrated in vacuo to give the title compound 13a (0.434 g) as a white solid.

Intermediate 13a:

HPLC: Column Chiralpack AD 25 cm×4.6 mm×5μ; mobile phase n-hexane/EtOH 8:2; flux=1 mL/min; λ=225 nm; retention time 10.7 minutes. Ratio 13a/13b=100:0.

Intermediate 14

2-(R)-(4-Fluoro-2-methyl-phenyl)-4-oxo-piperidine-1-carboxylic acid (3,5-dichlorobenzyl)-methylamide A saturated sodium hydrogen carbonate solution (15 mL) was added to a solution of intermediate 9 (1.0 g) in AcOEt (15 mL) and the resulting mixture was vigorously stirred for 15 minutes. The aqueous layer was back-extracted with further AcOEt (10 mL) and the collected organic phases were dried and concentrated in vacuo to give the free base 2-(R)4-fluoro-2-methyl-phenyl)-4-oxo-piperidine (0.550 g) as a yellow oil.

A solution of 2-(R)-(4-fluoro-2-methyl-phenyl)-4-oxo-piperidine (0.550 g) and TEA (20.5 mL) in AcOEt (5.5 HL) was added drop-wise, over 40 minutes, to a solution of triphosgene (0.385 g) in AcOEt (2.75 mL) previously cooled to 0° C. under a nitrogen atmosphere. The solution was allowed to warm to r.t. and stirred at 23° C. for 2 hours, then N-(3,5-dichloro)benzyl-methylamine hydrochloride (3.17 g) and TEA (1.860 mL) in AcOEt (8.25 mL) were added. The reaction mixture was stirred for 2 hours at 20° C., then it was washed with 10% sodium hydroxide solution (3×8 mL) and 1% hydrochloric acid solution (3×8 mL). The organic layer was dried and concentrated in vacuo to a residue which was purified through a silica pad (CH/AcOEt from 9/1 to 1/1) to give the title compound (0.870 g) as a colourless oil.

T.l.c.: CH/AcOEt 1:1, Rf=0.40. NMR (d$_6$-DMSO): δ (ppm) 7.45 (t, 1H); 7.29 (m, 1H); 7.07 (d, 2H); 7.0–6.94 (m, 2H); 5.16 (dd, 1H); 4.40–4.26 (dd, 2H); 3.55 (m, 2H); 2.76 (s, 3H); 2.75–2.6 (m, 2H); 2.5 (m, 2H); 2.29 (s, 3H).

Intermediate 15

3-Pyrazin-2-yl-propionic acid ethyl ester

Butyl lithium (2.5M in hexane—2560 mL) was added within 2 hours into a 10 L flask charged with THF (3350 mL) and diisopropylamine (658 g) while the temperature was maintained at 0–5° C. with an ice bath. The LDA solution was then precooled to −50° C. and a mixture of methylpyrazine (606 g) and THF (590 mL) was added within 2 hours under vigorous stirring at −40 to −30° C. The deep red anion solution is then pumped to a cooled (−60° C.) mixture of tert-butyl bromoacetate (1255 g) and THF (3360 mL) in a 20 L reactor. During the addition of the anion solution, the temperature in the reaction vessel did not exceed −55° C. After the addition, the mixture is stirred for further 30 min at −55° C. and then transferred to a 30 L reactor (the transesterification and removal of solvents can be done for two runs at once). A solution of sodium ethylate (142 g) dissolved in EtOH (2200 mL) was then added to the orange mixture and about 12 L of solvents were distilled off until a temperature of 80° C. was reached in the distillation head and 100° C. in the boiling liquid. The mixture was cooled to approximately 30° C. and then toluene (840 mL), AcOEt (840 mL), and water (1180 mL) were added. After separation of the phases, the organic layer was extracted three times with AcOEt (420 mL) and toluene (170 mL) each. The combined organic phases were then concentrated in vacuo and the residue was distilled over a Vigreux column (bp 115 to 130° C. @ 0.07 mbar) giving the title compound (579 g).

T.l.c.:CH/EtOAc=1:1, Rf=0.36. $^1$H-NMR (d$_6$-DMSO): δ (ppm) 8.57 (d, 1H); 8.52 (dd, 1H); 8.45 (d, 1H); 4.01 (q, 2H); 3.04 (t, 211); 2.76 (t, 2H); 1.12 (t, 3H). MS (ES/+): m/z=181 [M+H]$^+$ Intermediate 16

(8aS)-Hexahydro-pyrrolo[1,2-a]pyrazin-6-one S-(+)-O-acetylmandelate (enantiomer 1)

A solution of (S)-(+)-O-acetylmandelic acid (2.77 g) in acetone (12 mL) was added drop-wise to a solution of intermediate 12 (4 g) in acetone (28 mL) at 20° C. The resulting mixture was seeded to initiate the precipitation.

The obtained precipitate was stirred at 20° C. over 4 hours then filtered washing with acetone (12 mL). The solid was dried in vacuo at 40° C. for 18 hours to give the title compound (3.44 g) as a white solid.

HPLC: Column Chiralpack AD 25×4.6×5 μm; mobile phase n-hexane/EtOH=1:1; flow=1 ml/min; λ=210 nm; retention times title compound 5.42 min., (8aR) enantiomer 6.06 min. E.e.>94%.

$^1$H-NMR (d$_6$-DMSO): δ (ppm) 9.5 (broad, 1H); 7.42 (m, 2H); 7.32 (m, 3H); 5.62 (s, 1H); 3.79 (dd, 1H); 3.55 (m, 1H); 3.14–3.02 (2dd, 2H); 2.80 (dt, 1H); 2.52 (dt, 1H); 2.40 (t, 1H); 2.19 (m, 2H); 2.06 (s, 3H); 2.05 (m, 1H); 1.49 (m, 1H). MS (ES/+): m/z=141 [M+H−PhCH(OAc)COOH]$^+$.

Intermediate 17

(4-Fluoro-2-methyl-phenylimino)-acetic acid ethyl ester

A solution of ethyl glyoxalate (50% solution in toluene—40.8 mL) in toluene (180 mL) was heated to reflux for 1.5 hours under a Nitrogen atmosphere, in a flask equipped with a Dean Stark apparatus. Then, a solution of 4-fluoro-2-methyl-aniline (10 g) in dry toluene (20 mL) was slowly added. The mixture was heated to reflux for 3 hours, then it was concentrated in vacuo. The residue was purified by flash chromatography (toluene/CH/AcOEt 4:4:2) to give the title compound (13.06 g) as a yellow oil.

T.l.c.: toluene/CH/AcOEt 4:4:2, Rf=0.67. NMR (CDCl3): δ (ppm) 7.8 (s, 1H); 6.95 (d, 1H); 6.85 (d, 2H); 4.4 (q, 2H); 2.35 (s, 3H); 3.3 (t 3H). MS (ES/+): m/z=210 [M+H]$^+$.

Intermediate 18

1-(4-Fluoro-2-methyl-phenyl)-4-oxo-1,2,3-tetrahydro-pyridine-2-carboxylic acid ethyl ester Boron trifluoride etherate (1.22 mL) was added to a solution of intermediate 17 (2 g) in anhydrous DCM (20 mL) previously cooled to −78° C. under a Nitrogen atmosphere. After stirring for 15 minutes at −78° C., the 1-methoxy-3-trimethylsiloxy-1,3-butadiene (2.67 mL) was dropped over 45 minutes. The resulting solution was stirred at −78° C. for 2 hours, then TFA (0.74 mL) was added. The mixture was stirred at 0° C. for 15 minutes, then a saturated sodium hydrogen carbonate solution was added and the mixture was extracted with AcOEt (3×50 mL). The combined organic extracts were dried and concentrated in vacuo to give a residue, which was purified by flash chromatography (CH/AcOEt from 8:3 to 7:3) to give the title compound (1.5 g) as a pale yellow solid.

T.l.c.: CH/AcOEt 6:4, Rf=0.2. NMR (CDCl3): δ (ppm) 7.4 (dd, 1H); 7.1 (d, 1H); 7.0–6.8 (m, 2H); 5.15 (d, 1H); 4.4 (m, 1H); 4.1 (m, 2H); 3.1–2.85 (m, 2H); 2.4 (s, 3H); 1.15 (t, 3H).

Intermediate 19

1-(4-Fluoro-2-methyl-phenyl)-4-oxo-piperidine-2-carboxylic acid ethyl ester

L-selectride (1M solution in dry THF, 3.96 mL) was added drop-wise, over 1 hour, to a solution of intermediate 18 (1 g) in dry THF (30 mL) previously cooled to −78° C. under a Nitrogen atmosphere. After 1 hour, a saturated sodium hydrogen carbonate solution (20 mL) was added drop-wise and the solution was extracted with AcOEt (3×50 mL). The combined organic extracts were dried and concentrated in vacuo to a residue, which was purified by flash chromatography (CH/AcOEt 8:2) to give the title compound (810 mg) as a white solid.

T.l.c.: CH/AcOEt 6:4, Rf=0.6. NMR (CDCl3): δ (ppm) 7.4 (dd, 1H); 7.1 (dd, 1H); 6.9 (dd, 1H); 6.8 (dt, 1H); 4.2 (q, 2H); 4.15 (m, 1H); 3.6 (m, 1H); 3.2 (m, 1H); 2.8–2.7 (dd, 2H); 2.6 (m, 2H); 2.4 (s, 3H); 1.2 (t, 3H).

Intermediate 20

1-(4-Fluoro-2-methyl-phenyl)-4-oxo-piperidine-2-carboxylic acid

Lithium hydroxide monohydrate (241 mg) was added to a solution of intermediate 19 (300 mg) in MeOH (15 mL) and water (3 mL) and the resulting solution was stirred at 80° C. for 1 hour. The solution was allowed to cool to r.t. and extracted with Et2O. The aqueous layer was acidified until pH=6 with acetic acid and extracted with AcOEt (3×15 mL). The combined organic extractes were dried and concentrated in vacuo to give the title compound (230 mg) as yellow solid, which was used without any further purification in the next step.

MS (ES/+): m/z=252 [M+H]$^+$.

Intermediate 21

1-(4-Fluoro-2-methyl-phenyl)-4-oxo-piperidine-2-carboxylic acid, (3,5-bis-trifluoromethyl-benzyl)methylamide DIPEA (2.6 mL) and O-(benzotriazol-1-yl)-N,N,N'N'-tetramethyluronium hexafluorophosphate (2.48 g) were added to a solution of intermediate 20 (1.259 g) in anhydrous DMF (25 mL) under a Nitrogen atmosphere. After stirring 30 minutes, (3,5-bis-trifluoromethyl-benzyl)methylamine hydrochloride (1.62 g) was added and the mixture was stirred at r.t. for 16 hours. The reaction mixture was diluted with AcOEt (50 mL) and washed with a saturated ammonium chloride solution (30 mL), a saturated sodium hydrogen carbonate solution (30 mL) and brine (3×50 mL). The organic extracts were dried and concentrated in vacuo. The residue was purified by flash chromatography (CH/AcOEt 9:1) to give the title compound (1.59 g) as a dark yellow oil.

T.l.c.: CH/AcOEt 1:1, Rf=0.25. NMR (d$_6$-DMSO): δ (ppm) 8.03 (bs, 1H); 7.84 (bs, 2H); 7.03 (dd, 1H); 6.79 (dd, 1H); 6.64 (td, 1H); 4.80 (d, 1H); 4.67 (m, 1H); 4.29 (d, 1H); 3.55 (m, 1H); 3.04 (m, 1H); 2.74 (m, 1H); 2.5 (m, 1H); 2.4–2.2 (m, 2H); 2.40 (s, 3H); 2.38 (s, 3H). MS (ES/+): m/z=491 [M+H]$^+$.

EXAMPLE 1

2-(R)-(4-Fluoro-2-methyl-phenyl)-4-(R)-(6-oxo-hexahydro-pyrrolo[1,2-a]-pyrazin-2-yl)-piperidine-1-carboxylic acid (3,5-bis-trifluoromethyl-benzyl)-methylamide (1a) and 2-(R)-(4-Fluoro-2-methyl-phenyl)-4-(S)-(6-oxo-hexahydro-pyrrolo[1,2-a]-pyrazin-2-yl)-piperidine-1-carboxylic acid (3,5-bis-trifluoromethyl-benzyl)-methylamide (1b)

A solution of intermediate 12 (129 mg) in anhydrous acetonitrile (2 mL) was added to a solution of intermediate 10 (300 mg) in anhydrous acetonitrile (5 mL) under a Nitrogen atmosphere. The solution was stirred at r.t. for 15 minutes, then sodium triacetoxyborohydride (233 mg) was added. The mixture was stirred at 23° C. for 2 days. The solution was diluted with AcOEt (15 mL) and washed with a 5% sodium hydrogen carbonate solution (15 mL) and brine (10 mL). The organic layer was dried and concentrated in vacuo to a residue which was purified by flash chromatography (AcOEt/MeOH 8:2) to give two fractions:
1. example 1a (21.9 mg)
2. example 1b (48 mg).

Example 1a

T.l.c.:AcOEt/MeOH 8:2, Rf=0.38. NMR (d$_6$-DMSO): δ (ppm) 7.95 (bs, 1H); 7.71 (bs, 2H); 7.31 (dd, 1H); 6.94 (dd, 1H); 6.85 (dt, 1H); 4.89 (m, 1H); 4.55 (d, 1H); 4.41 (d, 1H); 3.78 (m, 1H); 3.52 (m, 1H); 3.35 (m, 1H); 3.14–3.05 (2m, 1H); 3.12 (m, 1H); 2.96–2.91 (2m, 1H); 2.81 (s, 3H); 2.74 (m, 1H); 2.62 (m, 1H); 2.26 (2s, 3H); 2.24 (m, 1H); 2.16 (m, 1H); 2.07 (m, 1H); 1.9 (m, 2H); 1.82 (m, 1H); 1.75 (m 1H); 1.72 (m, 2H, 1.51 (m, 1H). MS (ES/+) m/z=615 [M+H]$^+$.

Example 1b

T.l.c.:AcOEt/MeOH 8:2, Rf=0.28. NMR (d$_6$-DMSO): δ (ppm) 7.94 (s, 1H); 7.59 (s, 2H); 7.23 (dd, 1H); 6.89 (dd, 1H); 6.77 (dt, 1H); 4.62 (d, 1H); 4.36 (d, 1H); 4.14 (d, 1H); 3.73 (dd, 1H); 3.45 (m, 2H); 2.97 (dd, 1H); 2.9 (s, 3H); 2.81 (bt, 1H); 2.66 (m, 3H); 2.34 (s, 3H); 2.17 (m, 2H); 2.03 (m, 2H); 1.84 (m, 2H); 1.75 (bt, 1H); 1.65 (m, 1H); 1.5 (m, 1H); 1.39 (m, 1H). MS (FAB/NBA) m/z=615 [M+H]$^+$.

EXAMPLE 2

2-(R)-(4-Fluoro-2-methyl-phenyl)-4-(S)-(6-oxo-hexahydro-pyrrolo[1,2-a]-pyrazin-2-yl)-piperidine-1-carboxylic acid (3,5-bis-trifluoromethyl-benzyl)-methylamide hydrochloride A solution of example 1b (46 mg) in dry Et2O (2 mL) was treated with hydrochloric acid (1M in Et2O—0.083 mL) at 0° C. under a Nitrogen atmosphere. The resulting solution was stirred at 0° C. for 30 minutes, then it was concentrated in vacuo and the residue was triturated with pentane (2×3 mL) to give the title compound as a white solid (39.4 mg).

NMR (d$_6$-DMSO): δ (ppm) 10.34 (bs, 1H); 7.96 (bs, 1H); 7.6 (bs, 2H); 7.28 (m, 1H); 6.85 (m, 1H); 6.83 (m, 1H); 4.63 (d, 1H); 4.37 (bd, 1H); 4.22 (bd, 1H); 4.0 (bd, 1H); 3.88 (m, 1H); 3.7–3.2 (m, 6H); 2.94 (s, 3H); 2.4–2.0 (m, 4H); 2.35 (t, 3H); 2.34 (s, 3H); 1.95 (m, 2H); 1.8–1.5 (m, 2H). MS (ES/+) m/z=615 [M+H−HCl]$^+$.

EXAMPLES 3

2-(R)-(4-Fluoro-2-methyl-phenyl)-4-(R)-((8aS)-6-oxo-hexahydro-pyrrolo[1,2-a]-pyrazin-2-yl)piperidine-1-carboxylic acid (3,5-bis-trifluoromethyl-benzyl)-methylamide (3a) and 2-(R)-(4-Fluoro-2-methyl-phenyl-4-(S)-((8aS)-6-oxo-hexahydro-pyrrolo[1,2-a]-pyrazin-2-yl)-piperidine-1-carboxylic acid (3,5-bis-trifluoromethyl-benzyl)-methylamide (3b)

Intermediate 13a (259.3 mg) was added to a solution of intermediate 10 (550 mg) in anhydrous acetonitrile (10 mL) under a Nitrogen atmosphere. The solution was stirred at r.t. for 30 minutes, then sodium triacetoxyborohydride (474.8 mg) was added. The mixture was stirred at 23° C. for 8 hours. The solution was diluted with a 5% sodium hydrogen carbonate solution (15 mL) and extracted with AcOEt (3×25 mL). The combined organic extracts were dried and concentrated in vacuo to a residue which was purified by flash chromatography (AcOEt/MeOH 8:2) to give two fractions:
1. example 3a (177 mg)
2. example 3b (280 mg).

Example 3a

T.l.c.:AcOEt/MeOH 8:2, Rf=0.38. NMR (d$_6$-DMSO): δ (ppm) 7.96 (s, 1H); 7.72 (s, 2H); 7.31 (dd, 1H); 6.95 (dd, 1H); 6.86 (dt, 1H); 4.89 (t, 1H); 4.55 (d, 1H); 4.42 (d, 1H); 3.8 (d, 1H); 3.52 (m, 1H); 3.35 (m, 1H); 3.13 (m, 1H); 3.06 (m, 1H); 2.96 (m, 1H); 2.81 (s, 1H); 2.75 (m, 1H); 2.64 (m, 1H); 2.26 (s, 3H); 2.23–2.17 (m, 2H); 2.07 (m, 1H); 1.9 (m, 2H); 1.81–1.71 (m, 4H); 1.52 (m, 1H). MS (ES/+) m/z=615 [M+H]$^+$.

Example 3b

T.l.c.:AcOEt/MeOH 8:2, Rf=0.28. NMR (d$_6$-DMSO): δ (ppm) 7.94 (s, 1H); 7.59 (s, 2H); 7.23 (dd, 1H); 6.89 (dd, 1H); 6.77 (dt, 1H); 4.62 (d, 1H); 4.36 (d, 1H); 4.14 (d, 1H); 3.73 (dd, 1H); 3.45 (m, 2H); 2.97 (dd, 1H); 2.9 (s, 3H); 2.81

(bt, 1H); 2.66 (m, 3H); 2.34 (s, 3H); 2.17 (m, 2H); 2.03 (m, 2H); 1.84 (m, 2H); 1.75 (bt, 1H); 1.65 (m, 1H); 1.5 (m, 1H); 1.39 (m, 1H). MS (ES/+) m/z=615 [M+H]$^+$.

EXAMPLE 4

2-(R)(4-Fluoro-2-methyl-phenyl)-4-(R)-((8aS)-6-oxo-hexahydro-Pyrrolo[1,2-a]-pyrazin-2-yl)-piperidine-1-carboxylic acid (3,5-bis-trifluoromethyl-benzyl)-methylamide hydrochloride A solution of example 3a (50 mg) in dry Et2O (2 mL) was treated with hydrochloric acid (1M in Et2O—0.09 mL) at 0° C. under a Nitrogen atmosphere. The resulting solution was stirred at 0° C. for 10 minutes, then it was concentrated in vacuo and the residue was triturated with pentane (2×2 mL) to give the title compound as a white solid (50.8 mg).

NMR (d$_6$-DMSO): δ (ppm) 10.96 (bs, 1H); 7.99 (bs, 1H); 7.81 (bs, 2H); 7.39 (m, 1H); 7.01 (dd, 1H); 6.93 (m, 1H); 5.26 (t, 1H); 4.57 (d, 1H); 4.41 (d, 1H); 4.1–3.75 (bm, 2H); 3.7–3.5 (m, 4H); 3.2 (m, 1H); 3.16 (m, 1H); 2.95 (s, 1H); 2.86 (m, 1H); 2.73 (s, 3H); 2.23 (s, 3H); 2.5–2.1 (m, 5H); 1.71 (m, 1H); 1.6 (m, 1H); 1.25 (m, 1H). MS (ES/+) m/z=615 [M+H−HCl]$^+$.

EXAMPLE 5

2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid (3,5-bis-trifluoromethyl-benzyl)-methylamide hydrochloride A solution of example 3b (275 mg) in dry Et2O (5 mL) was treated with hydrochloric acid (1M in Et2O—0.5 mL) at 0° C. under a Nitrogen atmosphere. The resulting solution was stirred at 0° C. for 30 minutes, then it was concentrated in vacuo and the residue was triturated with pentane (2×3 mL) to give the title compound as a white solid (268 mg).

NMR (d$_6$-DMSO): δ (ppm) 11.1 (bs, 1H); 7.95 (bs, 1H); 7.6 (bs, 2H); 7.26 (dd, 1H); 6.94 (dd, 1H); 6.82 (m, 1H); 4.63 (d, 1H); 4.37 (d, 1H); 4.21 (dd, 1H); 3.97 (m, 2H); 3.55 (m, 4H); 3.21 (m, 1H); 2.93 (s, 3H); 2.85 (m, 2H); 2.75 (m, 1H); 2.32 (s, 3H); 2.4–2.1 (m, 5H); 1.97 (m, 1H); 1.69 (q, 1H); 1.57 (m, 1H). MS (ES/+) m/z=615 [M+H−HCl]$^+$. HPLC: Column Chiralpack AD 25 cm×4.6 mm×5μ; mobile phase n-hexane/EtOH 8:2; flux=1 mL/min; λ=225 nm; retention time 8.7 minutes.

EXAMPLES 6

2-(R)-(4-Fluoro-2-methyl-phenyl)-4-(R)-((8aR)-6-oxo-hexahydro-pyrrolo[1,2-a]-pyrazin-2-yl)-piperidine-1-carboxylic acid (3,5-bis-trifluoromethyl-benzyl)-methylamide (6a) and 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid (3,5-bis-trifluoromethyl-benzyl)-methylamide (6b)

A solution of intermediate 13b (3.1 g) in anhydrous acetonitrile (60+50 mL) was added to a solution of intermediate 10 (7.2 g) in anhydrous acetonitrile (40 mL) under a Nitrogen atmosphere. The solution was stirred at r.t. for 20 minutes, then sodium triacetoxyborohydride (5.6 g) was added. The mixture was stirred at 23° C. for 13 hours. The solution was diluted with a 5% sodium hydrogen carbonate solution (30 mL) and water (90 mL), stirred at 23° C. for 10 minutes, then concentrated in vacuo to eliminate the acetonitrile. The residue was extracted with AcOEt (2×200 mL). The combined organic extracts were washed with brine (300 mL), dried and concentrated in vacuo to a residue which was purified by flash chromatography (AcOEt/MeOH 8:2) to give two fractions:
1. example 6a (2.0 g)
2. example 6b (3.67 g).

Example 6a

T.l.c.:AcOEt/MeOH 8:2, Rf=0.49. NMR (d$_6$-DMSO): δ (ppm) 7.96 (bs, 1H); 7.72 (bs, 2H); 7.31 (bt, 1H); 6.95 (dd, 1H); 6.86 (dt, 1H); 4.89 (m, 1H); 4.55 (d, 1H); 4.42 (d, 1H); 3.78 (m, 1H); 3.53 (m, 1H); 3.35 (m, 1H); 3.14 (m, 2H); 2.92 (m, 1H); 2.82 (s, 3H); 2.75 (m, 1H); 2.63 (m, 1H); 2.27 (s, 3H); 2.23–2.17 (m, 2H); 2.08 (m, 1H); 1.91–1.7 (m, 6H); 1.52 (m, 1H). MS (ES/+) m/z=615 [M+H]$^+$.

Example 6b

T.l.c.:AcOEt/MeOH 8:2, Rf=0.33. NMR (d$_6$-DMSO): δ (ppm) 7.94 (s, 1H); 7.59 (s, 2H); 7.23 (dd, 1H); 6.89 (dd, 1H); 6.77 (dt, 1H); 4.62 (d, 1H); 4.36 (d, 1H); 4.14 (d, 1H); 3.73 (dd, 1H); 3.45 (m, 2H); 2.97 (dd, 1H); 2.9 (s, 3H); 2.81 (bt, 1H); 2.66 (m, 3H); 2.34 (s, 3H); 2.17 (m, 2H); 2.03 (m, 2H); 1.84 (m, 2H); 1.75 (bt, 1H); 1.65 (m, 1H); 1.5 (m, 1H); 1.39 (m, 1H). MS (ES/+) m/z=615 [M+H]$^+$.

EXAMPLE 7

2-(R)-(4-Fluoro-2-methyl-phenyl)-4-(R)-((8aR)-6-oxo-hexahydro-pyrrolo[1,2-a]-pyrazin-2-yl)-piperidine-1-carboxylic acid (3,5-bis-trifluoromethyl-benzyl)-methylamide hydrochloride A solution of example 6a (50 mg) in dry Et2O (2 mL) was treated with hydrochloric acid (1M in Et2O—0.09 mL) at 0° C. under a Nitrogen atmosphere. The resulting solution was stirred at 0° C. for 10 minutes, then it was concentrated in vacuo and the residue was triturated with pentane (2×2 mL) to give the title compound as a white solid (50.67 mg).

NMR (d$_6$-DMSO): δ(ppm) 10.96 (bs, 1H); 7.98 (bs, 1H); 7.81 (bs, 2H); 7.38 (m, 1H); 7.01 (dd, 1H); 6.93 (m, 1H); 5.26 (bt, 1H); 4.56 (d, 1H); 4.41 (d, 1H); 4.1–3.8 (bm, 2H); 3.67 (m, 2H); 3.49 (bd, 2H); 3.21 (m, 2H); 3.13 (m, 1H); 2.91 (m, 1H); 2.73 (s, 3H); 2.24 (s, 3H); 2.5–2.1 (m, 5H); 1.73 (m, 1H); 1.59 (m, 1H); 1.25 (m, 1H). MS (ES/+) m/z=615 [M+H−HCl]$^+$.

EXAMPLE 8

2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid (3,5-bis-trifluoromethyl-benzyl)-methylamide hydrochloride A solution of example 6b (3.0 g) in dry Et2O (30 mL) was treated with hydrochloric acid (1M in Et2O—5.37 mL) at 0° C. under a Nitrogen atmosphere. The resulting mixture was stirred at 0° C. for 1.5 hours, then pentane (5 mL) and the solid was filtered off. The precipitate was washed with pentane (20 mL), Et2O (5 mL) and further pentane (15+30 mL) to give the title compound as a white solid (3.1 g).

NMR (d$_6$-DMSO): δ (ppm) 11.06 (bs, 1H); 7.95 (bs, 1H); 7.6 (bs, 24); 7.27 (dd, 1H); 6.94 (dd, 1H); 6.82 (m, 1H); 4.63

(d, 1H); 4.37 (d, 1H); 4.22 (dd, 1H); 3.97 (m, 2H); 3.56 (m, 4H); 3.21 (m, 1H); 2.93 (s, 3H); 2.89 (m, 2H); 2.75 (m, 1H); 2.36 (s, 3l); 2.4–2.1 (m, 5H); 1.91 (m, 1H); 1.72 (q, 1H); 1.57 (m, 1H). MS (ES/+) m/z=615 [M+H−HCl]$^+$. HPLC: Column Chiralpack AD 25 cm×4.6 mm×5μ; mobile phase n-hexane/EtOH 8:2; flux=1 mL/min; λ=225 nm; retention time 9.5 minutes.

EXAMPLE 9

2-(R)-(4-Fluoro-2-methyl-phenyl)-4-(R)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (9a) and 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)(3,5-bis-trifluoromethyl-phenyl)-ethyl]-methylamide (9b)

Method A:

Intermediate 4a (168 mg) and sodium triacetoxyborohydride (127 mg) were added to a solution of intermediate 13a (80 mg) in anhydrous acetonitrile (4 mL) under a Nitrogen atmosphere. The mixture was stirred at 23° C. for 14 hours. The solution was diluted with a 5% sodium hydrogen carbonate solution (5 mL) and extracted with AcOEt (2×10 mL). The combined organic extracts were dried and concentrated in vacuo to a residue which was purified by flash chromatography (AcOEt/MeOH 9:1) to give three fractions:
1. example 9a (18 mg) a a white solid
2. mixture of example 9a and 9b (160 mg)
3. example 9b (8 mg) as a white solid.

Method B:

A solution of intermediate 13a (2.4 g) in anhydrous acetonitrile (80 mL) was added to a solution of intermediate 4a (5.7 g) in anhydrous acetonitrile (30 mL) under a Nitrogen atmosphere. Sodium triacetoxyborohydride (4.36 g) was added in three portions every 15 minutes and the mixture was stirred at 23° C. for 22 hours. The solution was diluted with water (75 mL) and a saturated sodium hydrogen carbonate solution (25 mL) and extracted with AcOEt (2×200 mL). The combined organic extracts were dried and concentrated in vacuo to a residue which was purified by flash chromatography (CH/AcOEt/MeOH 50:50:8) to give four fractions:
1. mixture example 9a and example 9b (1.27 g) in ratio 1:1
2. example 9b (1.66 g) (ratio 9a:9b=13:87)
3. example 9b (420 mg) (ratio 9a:9b=5:95)
4. example 9b (800 mg) (ratio 9a:9b=2:98)

Example 9a

T.l.c.:AcOEt/MeOH 8:2, Rf=0.55.MS (ES/+) m/z=1629 [M+H]$^+$. HPLC: Column Supelcosil ABZ Plus 25 cm×4.6 mm×5μ; mobile phase NH$_4$OAc 10 mmol/CH$_3$CN from 60:40 to 10:90 in 5 min. then NH$_4$OAc 10 mmol/CH$_3$CN for 10 min.; flux=0.8 mL/min; %=220 nm; retention time 9.27 minutes.

Example 9b

T.l.c.:AcOEt/MeOH 8:2, Rf=0.48. MS (ES/+) m/z=629 [M+H]$^+$. HPLC: Column Supelcosil ABZ Plus 25 cm×4.6 mm×5μ; mobile phase NH$_4$OAc 10 mmol/CH$_3$CN from 60:40 to 10:90 in 5 min. then NH$_4$OAc 10 mmol/CH$_3$CN for 10 min.; flux=0.8 mL/min; λ=220 nm; retention time 8.84 minutes.

EXAMPLE 10

2-(R)-(4-Fluoro-2-methyl-phenyl)-4-(R)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride A solution of example 9a (18 mg) in dry Et2O (1.3 mL) was treated with hydrochloric acid (1M in Et2O—32 μl) at 0° C. under a Nitrogen atmosphere. The resulting mixture was stirred at 0° C. for 30 minutes, then the mixture was concentrated in vacuo. The precipitate was washed with pentane (2 mL) to give the title compound as a white solid (17.6 mg).

NMR (d$_6$-DMSO): δ (ppm) 10.65 (bm, 1H); 7.99 (s, 1H); 7.76 (s, 2H); 7.37 (dd, 1H); 7.01 (dd, 1H); 6.93 (dd, 1H); 5.24 (bm, 1H); 5.04 (q, 1H); 4.0–3.95 (bm, 2H); 3.68 (m, 1H); 3.58 (m, 2H); 3.51 (m, 1H); 3.24–3.15 (m, 2H); 2.96 (m, 1H); 2.85 (m, 1H); 2.54 (s, 3H); 2.36–2.13 (m, 6H); 2.21 (s, 3H); 1.72 (m, 1H); 1.59 (m, 1H); 1.57 (d, 3H). MS (ES/+) m/z=629 [M+H−HCl]$^+$. HPLC: Column Supelcosil ABZ Plus 25 cm×4.6 mm×5μ; mobile phase NH$_4$OAc 10 mmol/CH$_3$CN from 60:40 to 10:90 in 5 min. then NH$_4$OAc 10 mmol/CH$_3$CN 10:90 for 10 min.; flux=70.8 mL/min; λ=220 nm; retention time 9.26 minutes.

EXAMPLE 11

2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride A solution of example 9b (8 mg) in dry Et2O (1 mL) was treated with hydrochloric acid (1M in Et2O —14 μL) at 0° C. under a Nitrogen atmosphere. The resulting mixture was stirred at 0° C. for 20 minutes, then the mixture was concentrated in vacuo. The precipitate was washed with pentane (2 mL) to give the title compound as a white solid (7.6 mg).

NMR (d$_6$-DMSO): δ (ppm) 10.22 (bs, 1H); 7.99 (s, 1H); 7.67 (s, 2H); 7.22 (dd, 1H); 6.94 (dd, 1H); 6.81 (t, 1H); 5.31 (q, 1H); 4.2 (dd, 1H); 4.0–3.86 (bm, 2H); 3.6–3.4 (m, 2H); 3.1–2.7 (m, 4H); 2.73 (s, 3H); 2.4–2.0 (m, 5H); 2.35 (s, 3H); 1.94 (m, 1H); 1.74 (q, 1H); 1.57 (d, 3H); 1.46 (d, 3H). MS (ES/+) m/z=629 [M+H−HCl]$^+$. HPLC: Column Supelcosil ABZ Plus 25 cm×4.6 mm×5μ, mobile phase NH$_4$OAc 10 mmol/CH$_3$CN from 60:40 to 10:90 in 5 min. then NH$_4$OAc 10 mmol/CH$_3$CN from 10:90 for 10 min.; flux=0.8 mL/min; λ=220 nm; retention time 8.86 minutes.

Column X-Terra 4.6×100 mm, RP18 3.5 μm; mobile phase: eluant A: NH$_4$HCO$_3$ 5 mM (pH=8)/CH$_3$CN 90/10—eluant B: NH$_4$HCO$_3$ 5 mM (pH=8)/CH$_3$CN 10/90—Gradient: from 50% B to 100% B in 7.5 min; 100% B for 0.5 min then 50% B for 3 min.; column temp.: 40° C.; flow=1 mL/min; λ=210 nm; retention time 4.15 minutes.

Example 11a 2-(R)-(4-Fluoro-2-methyl-phenyl-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride as anhydrous crystalline form A 2% sodium hydroxide solution (100 mL) was added to a suspension of example 11c(10 g) in AcOEt (150 mL). Then the two phases mixture were stirred for 10 minutes and the layers were separated. The organic phase was washed with water (100 mL) and then concentrated in vacuo up to 40 mL. AcOEt (100 mL) was added to the organic phase, which was then concentrated in vacuo a second time up to 40 mL. The solution was further diluted with AcOEt (60 mL) and 5–6N hydrochloric acid in isopropanol (3 mL) was added. After 5 minutes the clear solution was seeded. Precipitation occurred in a few minutes and after further 20 minutes stirring, n-heptane (100 mL) was added in 10–15 minutes. The obtained mixture was stirred 2 hours at 20° C. The solid was then filtered, washed with AOEt/n-heptane 1/1 (60 mL) and dried in vacuo at 40° C. for 16 hours to give the title compound (8.08 g) as a white solid.

X ray podwer diffraction data are reported in table 1

TABLE 1

The X-ray podwer diffraction pattern of the product of the Example 11a in terms of d spacing is as follows

| Angle(°2 Theta) | d value(A) |
|---|---|
| 3.412 | 25.87492 |
| 6.87 | 12.85613 |
| 9.867 | 8.95664 |
| 12.877 | 6.86899 |
| 14.274 | 6.19974 |
| 15.4 | 5.74895 |
| 16.732 | 5.29424 |
| 17.323 | 5.11486 |
| 17.966 | 4.93311 |
| 18.521 | 4.78656 |
| 19.557 | 4.53525 |
| 22.12 | 4.01529 |
| 22.382 | 3.96884 |
| 24.311 | 3.65818 |
| 27.117 | 3.28566 |
| 27.836 | 3.20239 |
| 28.374 | 3.14292 |
| 28.846 | 3.0925 |
| 29.372 | 3.03835 |
| 33.9 | 2.64214 |

Example 11b 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)ethyl]-methylamide hydrochloride as dihydrate crystalline form To a 265 mg of example 11a, 3 ml of water was added. The suspension was stirred overnight at 25° C. and then centrifuged for 5 min at 10000 rpm. The solid was filtered using a centrifugal filter device (Millipore Ultrafree-MC 0.45 μm) to obtain the title compound (250 mg).

X ray podwer diffraction data are reported in table 2

TABLE 2

The X-ray podwer diffraction pattern of the product of the Example 11b in terms of d spacing is as follows

| Angle(°2-Theta) | d value(A) |
|---|---|
| 3.233 | 27.30972 |
| 6.353 | 13.90157 |
| 12.14 | 7.28437 |
| 12.647 | 6.99378 |
| 13.282 | 6.6605 |
| 13.5 | 6.55347 |
| 15.48 | 5.71928 |
| 16.324 | 5.42557 |
| 16.779 | 5.27951 |
| 17.825 | 4.97188 |
| 19.022 | 4.66158 |
| 19.414 | 4.5685 |
| 19.901 | 4.45772 |
| 21.339 | 4.1605 |
| 21.915 | 4.05245 |
| 22.21 | 3.99923 |
| 23.161 | 3.83714 |
| 23.521 | 3.77915 |
| 24.179 | 3.67782 |
| 25.417 | 3.50136 |
| 26 | 3.42415 |
| 26.668 | 3.33994 |
| 28.052 | 3.17821 |
| 28.553 | 3.1236 |
| 29.551 | 3.0203 |
| 31.297 | 2.85568 |
| 32.8 | 2.72816 |
| 34.148 | 2.62353 |

Example 11c 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate Method A:

Intermediate 16 (25 g) was suspended in acetonitrile (300 mL), then TEA (10.4 mL) was quickly added in order to obtain the free base: the aspect of the slurry did not change as a new precipitate of TEA-acetylmandelate salt was formed. The mixture was kept under stirring for 15–20 minutes. Meanwhile intermediate 4a (25 g) was dissolved in acetonitrile (125 mL) and the so-obtained solution was quickly added to the slurry. Then Sodium triacetoxyborohydride (15 g) was added all at once and the mixture was kept under stirring conditions for 22 hours.

The white precipitate was filtered off and the mother liquors were evaporated to 100 mL. AcOEt (250 mL) was added to the so-obtained mixture and the resulting solution was washed with aqueous 4% sodium hydrogen carbonate solution (2×125 mL) and then with 5% sodium chloride solution (125 mL). The organic layer dried and evaporated to 100 mL. Isopropyl alcohol (150 ml) was added and the mixture was evaporated again to 100 mL. This operation was repeated. The final volume of the mixture was adjusted to 200 mL adding further isopropyl alcohol (100 mL). A solution of maleic acid (5.8 g) in isopropyl alcohol (50 mL) was dropped in ca. 10 minutes. The mixture was seeded and precipitation occurred in few minutes. The slurry was stirred 1 hour at 20° C. and isoctane (250 mL) was added in 10 minutes. The resulting suspension was stirred at room temperature for 22 hours. The solid was filtered and washed with isopropanol/isoctane 1/1 (150 mL) and dried in vacuo at 40° C. for 18 hours giving the title compound (13.75 g) as a white solid.

Method B:

Intermediate 16 (1 g) was suspended in acetonitrile (12 mL), then TEA (0.415 mL) was quickly added in order to obtain the free base: the aspect of the slurry did not change as a new precipitate of TEA-acetylmandelate salt was formed. After 30 minutes of stirring, the mixture was treated with sodium triacetoxyborohydride (0.6 g) plus formic acid (0.224 mL).

Meanwhile intermediate 4a (1 g) was dissolved in acetonitrile (6 mL) and the so-obtained solution was quickly added to the slurry and the resulting mixture was kept under stirring conditions for 18 hours. The slurry was evaporated to small volume. AcOEt (10 mL) was added to the so-obtained mixture and the resulting solution was washed with aqueous 4% sodium hydrogen carbonate (2×5 mL) and then with 5% sodium chloride solution (5 mL). The organic layer was dried and evaporated to a white foam.

Isopropyl alcohol (10 mL) was added and the mixture was evaporated again to dryness. The resulting foam was, once again, dissolved in isopropyl alcohol (8 mL) and treated drop-wise with a solution of maleic acid (0.232 g) in isopropyl alcohol (2 mL). After 30 minutes the mixture was seeded and precipitation occurred in a few minutes. The slurry was stirred 1 hour at 20° C. and then isoctane (10 mL) was added dropwise over 5–10 minutes. The resulting suspension was stirred at room temperature for 19 hours. The solid was filtered and washed with isopropanol/isoctane 1/1 (5 mL) and dried in vacuo at 40° C. for 18 hours giving the title compound (0.639 g) as a white solid.

HPLC: Column X-Terra 4.6×100 mm, RP18 3.5 μm; mobile phase: eluant A: $NH_4HCO_3$ 5 mM (pH=8)/$CH_3CN$ 90/10—eluant B: $NH_4HCO_3$ 5 mM (pH=8)/$CH_3CN$ 10/90—Gradient: from 50% B to 100% B in 7.5 minutes; 100% B for 0.5 minutes then 50% B for 3 minutes; column temp. 40° C.; flow=1 mL/min; λ=210 nm; retention times 4.15 minutes, >99% a/a $^1$H-NMR ($d_6$-DMSO): δ (ppm) 7.98 (bs, 1H); 7.68 (bs, 2H); 7.21 (dd, 1H); 6.93 (dd, 1H); 6.81 (dt, 1H); 6.09 (s, 2H); 5.31 (q, 1H); 4.19 (dd, 1H); 3.93 (m, 1H); 3.74 (bm, 1H); 3.46 (m, 1H); 3.45 (bm, 1H); 3.30 (bm, 2H); 2.93 (bt, 1H); 2.79 (t, 1H); 2.73 (s, 3H); 2.73 (bm, 1H); 2.60 (bm, 1H); 2.35 (s, 3H); 2.23 (m, 2H); 2.12 (m, 1H); 2.04 (bd, 1H); 1.98 (bd, 1H); 1.84 (m, 1H); 1.64 (q, 1H); 1.56 (m, 1H); 1.46 (d, 3H). MS (ES/+): m/z=629 [MH−HOOCCHCHCOOH]$^+$.

EXAMPLE 12

2-(R)-(4-Fluoro-2-methyl-phenyl)-4-(R)-((8aR)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (12a) and 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid [1-(R)(3,5-bis-trifluoromethyl-phenyl)-ethyl]-methylamide (12b)

Method A:

Intermediate 13b (220 mg) was added to a solution of intermediate 4a (504 mg) in anhydrous acetonitrile (10 mL) under a Nitrogen atmosphere. The solution was stirred at r.t. for 15 minutes, then sodium triacetoxyborohydride (422 mg) was added. The mixture was stirred at 23° C. for 18 hours. The solution was diluted with a 5% sodium hydrogen carbonate solution (5 mL) and extracted with AcOEt (3×30 mL). The combined organic extracts were dried and concentrated in vacuo to a residue which was purified by flash chromatography (AcOEt/MeOH 9:1) to give three fractions:
1. example 12a (125 mg) as a white solid.
2. mixture of example 12a and 12b (950 mg)
3. example 12b (280 mg) as a white solid.

Method B:

Intermediate 4a (10.45 g) and sodium triacetoxyborohydride (6.32 g) were added to a solution of intermediate 13b (4.35 g) in anhydrous acetonitrile (200 mL) under a Nitrogen atmosphere. The mixture was stirred at 23° C. for 14 hours. The solution was diluted with water (50 mL) and with a saturated solution of sodium hydrogen carbonate (30 mL) and extracted with AcOEt (3×100 mL). The combined organic extracts were dried and concentrated in vacuo to a residue which was purified by flash chromatography (CH/AcOEt/MeOH 50:50:8) to give these fractions as white foams:
1. mixture 12a and 12b (1 g) (ratio 12a:12b=75:25)
2. mixture 12a and 12b (2.65 g) (ratio 12a:12b=50:50)
3. example 12b (2.13 g)—(ratio 12a:12b=16:84)
4. example 12b (1.4 g) (ratio 12a:12b=6:94)
5. mixture of 12a and 12b (0.5 g) (ratio 12a:12b=30:70)
6. example 12a (1.6 g) (ratio 12a:12b=95:5)

Example 12a

T.l.c.:AcOEt/MeOH 9:1, Rf=0.24.MS (ES/+) m/z=629 [M+H]$^+$. HPLC: Column Supelcosil ABZ Plus 25 cm×4.6 mm×5μ; mobile phase $NH_4OAc$ 10 mmol/$CH_3CN$ from 60:40 to 10:90 in 5 min. then $NH_4OAc$ 10 mmol/$CH_3CN$ 10:90 for 10 min.; flux=0.8 mL/min.; λ220 nm; retention time 9.28 minutes.

Example 12b

T.l.c.:AcOEt/MeOH 9:1, Rf=0.2.MS (ES/+) m/z=629 [M+H]$^+$. HPLC: Column Supelcosil ABZ Plus 25 cm×4.6 mm×5μ; mobile phase $NH_4OAc$ 10 mmol/$CH_3CN$ from 60:40 to 10:90 in 5 min. then $NH_4OAc$ 10 mmol/$CH_3CN$ 10:90 for 10 min.; flux=0.8 mL/min; λ=220 nm; retention time 8.86 minutes.

EXAMPLE 13

2-(R)-(4-Fluoro-2-methyl-phenyl)-4-(R)-((8aR)-6-oxo-hexahydro-pyrrolo[1,2-a]-pyrazin-2-yl)-piperidine-1-carboxylic acid [1-(R)(3,5-bis-trifluoromethyl-phenyl)ethyl]-methylamide hydrochloride A solution of example 12a (125 mg) in dry Et2O (3 mL) was treated with hydrochloric acid (1M in Et2O—201 μL) at 0° C. under a Nitrogen atmosphere. The resulting mixture was stirred at 0° C. for 15 minutes, then the mixture was concentrated in vacuo. The precipitate was triturated twice with Et2O/pentane 2:1 (2 mL) to give the title compound as a white solid (115 mg).

NMR ($d_6$-DMSO): δ (ppm) 10.9–10.6 (bm, 1H); 7.99 (s, 1H); 7.76 (s, 2H); 7.36 (dt, 1H); 7.0 (dd, 1H); 6.92 (dt, 1H); 5.25 (bt, 1H); 5.05 (q, 1H); 3.98 (m, 2H); 3.67 (m, 2H); 3.58 (m, 1H); 3.44 (m, 1H); 3.2 (m, 2H); 2.9 (m, 2H); 2.53 (s, 3H); 2.22 (s, 3H); 2.42.1 (m, 6H); 1.73 (m, 1H); 1.56 (m, 1H); 1.56 (d, 3H). MS (ES/+) m/z=629 [M+H−HCl]$^+$.

EXAMPLE 14

2-(R)-(4-Fluoro-2-methyl-phenyl)-4-(S)-((8aR)-6-oxo-hexahydro-pyrrolo[1,2-a]-pyrazin-2-yl)piperidine-1-carboxylic acid [1-(R)-(3,5-bis-trifluoromethyl-phenyl)ethyl]-methylamide hydrochloride A solution of example 12b (280 mg) in dry Et2O (5 mL) was treated with hydrochloric acid (1M in Et2O—473 μL) at 0° C. under a Nitrogen atmosphere. The resulting mixture was stirred at 0° C. for 15 minutes, then the mixture was concentrated in vacuo. The precipitate was triturated twice with Et2O/pentane 2:1 (2 mL) to give the title compound as a white solid (245 mg).

NMR (d$_6$-DMSO): δ (ppm) 11.05 (bs, 1H); 7.95 (s, 1H); 7.64 (s, 2H); 7.19 (dt, 1H); 6.9 (dd, 1H); 6.78 (dt, 1H); 5.28 (q, 1H); 4.16 (dd, 1H); 3.53 (m, 2H); 3.41 (m, 2H); 3.17 (t, 1H); 2.94 (m, 2H); 2.96–2.8 (m, 2H); 2.75 (t, 1H); 2.69 (s, 3H); 2.31 (s, 3H); 2.3–2.0 (m, 1H); 1.9 (m, 1H); 1.75 (q, 1H); 1.5 (m, 1H); 1.43 (d, 3H). MS (ES/+) m/z=629 [M+H–HCl]$^+$.

EXAMPLE 15

2-(R)-(4-Fluoro-2-methyl-phenyl)-4-(R)-((8aS)-6-oxo-hexahydro-pyrrolo[1,2-a]-pyrazin-2-yl)-piperidine-1-carboxylic acid [1-(S)-(3,5-bis-trifluoromethyl-phenyl)ethyl]-methylamide (15a) and 2-(R)-(4-Fluoro-2-methyl-phenyl)-4-(S)-((8aS)-oxo-hexahydro-pyrrolo[1,2-a]-pyrazin-2-yl)-piperidine-1-carboxylic acid [1-(S)-(3,5-bis-trifluoromethyl-phenyl)ethyl]-methylamide (15b)

Intermediate 13a (250 mg) was added to a solution of intermediate 5b (449 mg) in anhydrous acetonitrile (9 mL) under a Nitrogen atmosphere. The solution was stirred at r.t. for 1 hour, then sodium triacetoxyborohydride (282 mg) was added. The mixture was stirred at 23° C. for 16 hours. The solution was diluted with a 5% sodium hydrogen carbonate solution (10 mL) and extracted with AcOEt (3×30 mL). The combined organic extracts were washed with brine (10 mL), dried and concentrated in vacuo to a residue which was purified by flash chromatography (AcOEt/MeOH 8:2) to give three fractions:
1. example 15a (181 mg) as a white solid.
2. mixture of example 15a and 15b (40 mg)
3. example 15b (218 mg) as a white solid.

Example 15a

T.l.c.:AcOEt/MeOH 8:2, Rf=0.46.MS (ES/+) m/z=629 [M+H]$^+$.

Example 15b

T.l.c.:AcOEt/MeOH 8:2, Rf=0.24. NMR (d$_6$-DMSO): δ (ppm) 1.45 (m, 1H); 1.47 (d, 3H); 1.65 (m, 1H); 1.70 (m, 1H); 1.85 (m, 1H); 1.9 (m, 1H); 1.95 (m, 1H); 2.00 (m, 1H); 2.05 (m, 1H); 2.25 (m, 2H); 2.34 (s, 3H); 2.65 (m, 1H); 2.77 (m, 1H); 2.80 (m, 1H); 2.81 (s, 3H); 3.40 (m, 1H); 3.41 (m, 1); 3.46 (dd, 1H); 3.74 (m, 2H); 4.13 (dd, 1H); 5.33 (q, 1H); 6.74 (m, 1H); 6.88 (dd, 1H); 7.54 (s, 2H); 7.20 (dd, 1H); 7.93 (s, 2H). MS (ES/+) m/z=629 [M+H]$^+$.

EXAMPLE 16

2-(R)-(4-Fluoro-2-methyl-phenyl)-4-(S)-(8aS)-6-oxo-hexahydro-pyrrolo[1,2-a]-pyrazin-2-yl)-piperidine-1-carboxylic acid [1-(S)-(3,5-bis-trifluoromethyl-phenyl)-ethyl]-methylamide (15b)

A solution of example 15b (218 mg) in dry Et2O (1 mL) was treated with hydrochloric acid (1M in Et2O—380 μL) at 0° C. under a Nitrogen atmosphere. The resulting mixture was stirred at 0° C. for 1 hour, then the mixture was concentrated in vacuo. The precipitate was triturated twice with pentane to give the title compound as a white solid (195 mg).

NMR (d$_6$-DMSO): δ (ppm) 10.60 (5b, 1H); 7.94 (s, 1H); 7,54 (s,2H); 7.22 (dd, 1H); 6.93 (dd, 1H); 6.80 (td, 1H); 5.33 (q, 1H); 4.20 (bd, 1H); 3.98 (bd, 1H); 3.92 (m, 1H); 3.60 (m, 1H); 3.46 (m, 1H); 3,53 (m, 1H); 3.43 (m, 1H); 3.14 (bt, 1H); 2.96 (m, 1H); 2.86 (m, 1H); 2.85 (s, 3H); 2.6 (s, 3H); 2.73 (m, 1H); 2.2–2.35 (m, 2H); 2.19 (m, 1H); 2.15 (m, 1H); 2.16 (m, 1H); 1.95 (dd, 1H); 1.64 (dd, 1H); 1.58 (m, 1H); 1.50 (d, 3H).

EXAMPLE 17

2-(R)-(4-Fluoro-2-methyl-phenyl)-4-(R)-((8aR)-oxo-hexahydro-pyrrolo[1,2-a]-pyrazin-2-yl)-piperidine-1-carboxylic acid [1-(S)-(3,5-bis-trifluoromethyl-phenyl)-ethyl]-methylamide (17a) and 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid [1-(S)-(3,5-bis-trifluoromethyl-phenyl)-ethyl]-methylamide (17b)

Intermediate 13b (220 mg) was added to a solution of intermediate 5b (500 mg) in anhydrous acetonitrile (10 mL) under a Nitrogen atmosphere. The solution was stirred at r.t. for 30 minutes, then sodium triacetoxyborohydride (422 mg) was added. The mixture was stirred at 23° C. for 18 hours. The solution was diluted with a 5% sodium hydrogen carbonate solution (5 mL) and extracted with AcOEt (3×30 mL). The combined organic extracts were washed with brine (10 mL), dried and concentrated in vacuo to a residue which was purified by flash chromatography (AcOEt/MeOH 8:2) to give two fractions:
1. example 17a (160 mg) as a white solid.
2. example 17b (243 mg) as a white solid.

Example 17a

T.l.c.:AcOEt/MeOH 8:2, Rf=0.21. NMR (d$_6$-DMSO): δ (ppm) 1.50 (d, 3H); 1.53 (m, 1H); 1.71 (m, 1H); 1.72 (m, 1H); 1.75 (m, 1H); 1.81 (m, 1H); 1.88 (m, 1H); 1.94 (m, 1H); 2.09 (m, 1H); 2.19 (m, 2H); 2.26 (s, 3H); 2.64 (m, 1H); 2.71 (s, 3H); 2.76 (m, 1H); 2.93 (m, 1H); 3.08 (m, 1H); 3.15 (m, 1H); 3.27 (m, 1H); 3.53 (m, 1H); 3.74 (m, 2H); 3.88 (bm, 1H); 4.85 (dd, 1H); 5.27 (q, 1H); 6.84 (td, 1H); 6.94 (dd, 1H); 7.30 (dd, 1H); 7.69 (s, 2H); 7.95 (s, 1H).

Example 17b

T.l.c.:AcOEt/MeOH 8:2, Rf=0.13. NMR (d$_6$-DMSO): δ (ppm) 1.45 (d, 3H); 1.6–2.27 (bm, 10H); 2.3 (s, 3H); 2.61–2.97 (bm, 4H); 2.78 (s, 3H); 2.9 (bd, 1H); 3.4 (d, 2H); 3.7–3.9 (bm, 1H); 4.1 (dd, 1H); 5.27 (q, 1H); 6.72 (td, 1H); 6.84 (dd, 1H); 7.15–7.19 (dd, 1H); 7.5 (s, 2H); 7.89 (s, 1H).

EXAMPLE 18

2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid [1-(S)-(3,5-bis-trifluoromethyl-phenyl)-ethyl]-methylamide A solution of example 17b (235 mg) in dry Et2O (4.2 mL) was treated with hydrochloric acid (1M in Et2O—411 µL) at 0° C. under a Nitrogen atmosphere. The resulting mixture was stirred at 0° C. for 15 minutes, then the mixture was concentrated in vacuo. The precipitate was triturated three times with pentane to give the title compound as a white solid (243 mg).

NMR ($d_6$-DMSO): δ (ppm) 10.88 (bs, 1H); 7.94 (s, 1H); 7.54 (s, 1H); 7.23 (dd, 1H); 6.93 (dd, 1H); 6.79 (td, 1H); 5.33 (q, 1H); 4.21 (dd, 1H); 3.99 (bs, 1H); 3.97 (m, 1H); 3.55 (m, 1H); 3.54–2.7 (m, 1H); 3,57 (m, 1H); 3.44 (m, 1H); 3.18 (t, 1H); 2.95 (m, 1H); 2.84 (s, 3H); 2.7 (t, 1H); 2.36 (s, 3H); 2.3 (m, 1H); 2.17 (m, 1H); 2.15 (q, 1H); 2.1 (m, 1H); 1.69 (q, 1H); 1.56 (m, 1H); 1.50 (d, 3H).

EXAMPLES 19

2-(R)-(4-Fluoro-2-methyl-phenyl)-4-(R)-((8aS)-oxo-hexahydro-pyrrolo[1,2-a]-pyrazin-2-yl)-piperidine-1-carboxylic acid (3,5-dichloro-benzyl)-methylamide (19a) and 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid (3,5-dichloro-benzyl)methylamide (19b)

Intermediate 13a (40 mg) was added to a solution of intermediate 14 (100 mg) in anhydrous acetonitrile (5 mL) under a Nitrogen atmosphere. The solution was stirred at r.t. for 15 minutes, then sodium triacetoxyborohydride (90 mg) was added. The mixture was stirred at 23° C. for 20 hours. The solution was diluted with a saturated sodium hydrogen carbonate solution (10 mL) and extracted with AcOEt (3×50 mL). The combined organic extracts were dried and concentrated in vacuo to a residue which was purified by flash chromatography (AcOEt/MeOH 8:2) to give two fractions:
1. example 19a (25 mg)
2. example 19b (40 mg).

Example 19a

T.l.c.:AcOEt/MeOH 8:2, Rf=0.36.MS (ES/+) m/z=547 [M+H]$^+$.

Example 19b

T.l.c.:AcOEt/MeOH 8:2, Rf=0.2.MS (ES/+) m/z=547 [M+H]$^+$.

EXAMPLE 20

2-(R)-(4-Fluoro-2-methyl-phenyl)-4-(R)-((8aS)-6-oxo-hexahydro-pyrrolo[1,2-a]-pyrazin-2-yl)-piperidine-1-carboxylic acid (3,5-dichloro-benzyl)-methylamide hydrochloride A solution of example 19a (25 mg) in dry Et2O (1 mL) was treated with hydrochloric acid (1M in Et2O—54 µL) at 0° C. under a Nitrogen atmosphere. The resulting mixture was stirred at 0° C. for 15 minutes, then the mixture was concentrated in vacuo. The precipitate was triturated with Et2O/pentane 1:1 and then pentane to give the title compound as a white solid (20 mg).

NMR ($d_6$-DMSO): δ (ppm) 10.95 (bs, 1H); 7.44 (s, 2H); 7.35 (m, 2H); 7.00 (s, 1H); 6.85 (m, 1H); 5.2–4.8 (m, 1H); 4.44.2 (dd, 2H); 4.05–3.5 (m, 10H); 3.2–1.5 (m, 8H); 2.7 (s, 3H); 2.27 (s, 3H). MS (ES/+) m/z=547 [M+H−HCl]$^+$.

EXAMPLE 21

2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid (3,5-dichloro-benzyl)methylamide hydrochloride A solution of example 19b (40 mg) in dry Et2O (1 mL) was treated with hydrochloric acid (1M in Et2O—87 µL) at 0° C. under a Nitrogen atmosphere. The resulting mixture was stirred at 0° C. for 15 minutes, then the mixture was concentrated in vacuo. The precipitate was triturated with Et2O/pentane 1:1 and then pentane to give the title compound as a white solid (35 mg).

NMR ($d_6$-DMSO): δ (ppm) 10.95 (bs, 1H); 7.44 (t, 1H); 7.28 (dd, 1H); 6.96 (dd, 1H); 6.93 (td, 1H); 6.89 (s, 2H); 4.49 (d, 1H); 4.19 (d, 1H); 4.16 (d, 1H); 3.97 (m, 2H); 3.6 (dd, 1H); 3.54 (m, 1H); 3.51 (dd, 1H); 3.46 (m, 1H); 3.19 (dd, 1H); 2.94 (m, 1H); 2.90 (s, 3H); 2.86 (dd, 1H); 2.37 (s, 3H); 2.26 (m, 1H); 2.24 (dd, 1H); 2.23 (dd, 1H); 2.17 (m, 1H); 1.96 (dd, 1H); 1.69 (dd, 1H); 1.58 (m, 1H). MS (ES/+) m/z=547 [M+H−HCl]$^+$.

EXAMPLES 22

2-(R)-(4-Fluoro-2-methyl-phenyl)-4-(R)-((8aR)-6-oxo-hexahydro-pyrrolo[1,2-a]-pyrazin-2-yl)-Piperidine-1-carboxylic acid (3,5-dichloro-benzyl)-methylamide (22a) and 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid (3,5-dichloro-benzyl)methylamide (22b)

Intermediate 13b (40 mg) was added to a solution of intermediate 14 (100 mg) in anhydrous acetonitrile (5 mL) under a Nitrogen atmosphere. The solution was stirred at r.t. for 15 minutes, then sodium triacetoxyborohydride (90 mg) was added. The mixture was stirred at 23° C. for 20 hours. The solution was diluted with a saturated sodium hydrogen carbonate solution (10 mL) and extracted with AcOEt (3×50 mL). The combined organic extracts were dried and concentrated in vacuo to a residue which was purified by flash chromatography (AcOEt/MeOH 8:2) to give two fractions:
1. example 22a (23 mg)
2. example 22b (43 mg).

Example 22a

T.l.c.:AcOEt/MeOH 8:2, Rf=0.36.MS (ES/+) m/z=547 [M+H]$^+$.

Example 22b

T.l.c.:AcOEt/MeOH 8:2, Rf=2.MS (ES/+) m/z=547 [M+H]$^+$.

EXAMPLE 23

2-(R)-(4-Fluoro-2-methyl-phenyl)-4-(R)-((8aR)-6-oxo-hexahydro-pyrrolo[1,2-a]-pyrazin-2-yl)-piperidine-1-carboxylic acid (3,5-dichloro-benzyl)methylamide hydrochloride A solution of example 22a (23 mg) in dry Et2O (2 mL) was treated with hydrochloric acid (1M in Et2O—46 μL) at 0° C. under a Nitrogen atmosphere. The resulting mixture was stirred at 0° C. for 1 hour, then the mixture was concentrated in vacuo. The precipitate was triturated with pentane to give the title compound as a white solid (25 mg).
NMR ($d_6$-DMSO): δ (ppm) 10.77 (bs, 1H); 7.48 (t, 1H); 7.37 (dd, 1H); 7.14 (m, 2H); 7.03 (dd, 1H); 6.96 (td, 1H); 5.23 (m, 1H); 4.33 (d, 1H); 4.28 (d, 1H); 3.99 (m, 1H); 3.98 (m 1H); 3.7 (dd, 1H); 3.63 (m, 1H); 3.6 (dd, 1H); 3.49 (m, 1H); 3.19 (t, 1H); 3.14 (dd, 1H); 2.93 (m, 1H); 2.71 (s, 3H); 2.4–2.2 (m, 2H); 2.35 (m, 1H); 2.27 (s, 3H); 2.22 (m, 1H); 2.18 (m, 1H); 2.17 (m, 1H); 1.75 (m, 1H); 1.6 (m, 1H). MS (ES/+) m/z=547 [M+H−HCl]$^+$.

EXAMPLE 24

2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid (3,5-dichloro-benzyl)-methylamide hydrochloride A solution of example 22b (41 mg) in dry Et2O (1 mL) was treated with hydrochloric acid (1M in Et2O—46 μL) at 0° C. under a Nitrogen atmosphere. The resulting mixture was stirred at 0° C. for 15 minutes, then the mixture was concentrated in vacuo. The precipitate was triturated with Et2o/pentane 1:1 and then pentane to give the title compound as a white solid (21 mg).
NMR ($d_6$-DMSO): δ (ppm) 10.72 (bs, 1H); 7.44 (t, 1H); 7.30 (dd, 1H); 6.96 (dd, 1H); 6.91 (m, 1H); 6.89 (s, 2H); 4.49 (d, 1H); 4.21 (m, 1H); 4.16 (d, 1H); 3.98 (m, 1H); 3.94 (m, 1H); 3.58 (dd, 1H); 3.56 (m, 1H); 3.5 (dd, 1H); 3.44 (m, 1H); 3.17 (t, 1H); 2.95 (m, 1H); 2.90 (s, 3H); 2.88 (dd, 1H); 2.74 (dd, 1H); 2.37 (s, 3H); 2.26 (m, 2H); 2.18 (m, 1H); 2.17 (m, 1H); 2.16 (m, 1H); 1.94 (m, 1H); 1.72 (m, 1H); 1.58 (m, 1H). MS (ES/+) m/z=547 [M+H−HCl]$^+$.

EXAMPLES 25

1-(4-Fluoro-2-methyl-phenyl)-4-((8aR)-6-oxo-hexahydro-pyrrolo[1,2-a]-pyrazin-2-yl)-piperidine-2-carboxylic acid (3,5-bis-trifluoromethyl-benzyl) methyl-amide (25a—anti) and 1-(4-Fluoro-2-methyl-phenyl)-4-((8aR)-6-oxo-hexahydro-pyrrolo[1,2-a]pyrazin-2-yl)-piperidine-2-carboxylic acid (3,5-bis-trifluoromethyl-benzyl)-methyl-amide (25b—syn)

Intermediate 13b (10 mg) was added to a solution of intermediate 21 (150 mg) in dry acetonitrile (1 mL) under a nitrogen atmosphere. The mixture was stirred at 23° C. for 30 minutes, then sodium triacetoxyborohydride (24 mg) was added. The solution was stirred at 23° C. for 16 hours, then washed with a 5% sodium hydrogen carbonate solution (5 mL) and brine (5 mL). The organic layer was dried and concentrated in vacuo to a residue which was purified by flash chromatography (AcOEt/MeOH 8:2) to give three fractions:
1. example 25a (C-2 and C-4 anti configuration—6.5 mg).
2. example 25a+example 25b (5.5 mg).
3. example 25b (C-2 and C-4 syn configuration-7.3 mg).

Example 25a

T.l.c.: AcOEt/MeOH 8:2, Rf=0.52.MS (ES/+) m/z=615 [M+H]$^+$.

Example 25a

T.l.c.: AcOEt/MeOH 8:2, Rf=0.39.MS (ES/+) m/z=615 [M+H]$^+$.

EXAMPLE 26

1-(4-Fluoro-2-methyl-phenyl)-4-((8aR)-6-oxo-hexahydro-pyrrolo[1,2-a]-pyrazin-2-yl)-piperidine-2-carboxylic acid (3,5-bis-trifluoromethyl-benzyl)-methyl-amide hydrochloride (25b—syn)

Example 25b (5.4 mg) in dry Et2O (0.5 mL) was treated with hydrochloric acid (1M in Et2O—0.1 mL) and the resulting solution was stirred at 0° C. for 30 minutes. The solution was concentrated in vacuo. The residue was triturated with Et2O (1 mL) and pentane (1 mL) to give the title compound as a white solid (4 mg).
NMR ($d_6$-DMSO): δ (ppm) 1.63 (m,1H); 1.88 (mb, 1H); 2.09 (mb, 1H); 2.19 (m,1H); 2.27 (s, 3H), 2.1–3.8 (13H); 3.11 (s, 3H); 3.95 (mb 1H), 4.02 (bd, 1H); 4.35 (5b, 1H); 4.94 (mb, 1H); 6.91 (dd, 1H); 6.73 (td, 1H); 7.55 (s, 2H); 7.93 (s, 1H); 7.10 (dd, 1H); 10.51 (bs, 1H).

EXAMPLE 27

1-(4-Fluoro-2-methyl-phenyl)-4-((8aS)-6-oxo-hexahydro-pyrrolo[1,2-a]pyrazin-2-yl)piperidine-2carboxylic acid (3,5-bis-trifluoromethyl-benzyl)-methyl-amide (25b—syn)

A solution of intermediate 21 (63 mg) in anhydrous acetonitrile (2 mL) was added to a solution of intermediate 13a (27 mg) in anhydrous acetonitrile (2 mL) under a nitrogen atmosphere. The mixture was stirred at 23° C. for 1 hour, then sodium triacetoxyborohydride (49 mg) was added. The solution was stirred at 23° C. for 24 hours, then further sodium triacetoxyborohydride (13.6 mg) was added and stirring was continued for 7 days. The mixture was diluted with DCM and washed with a saturated sodium hydrogen carbonate solution. The organic layer was dried and concentrated in vacuo to a residue which was purified by flash chromatography (AcOEt/MeOH 9:1) to give the title compound (14 mg) as a white foam.
T.l.c.: AcOEt/MeOH 8:2, Rf=0.28. NMR ($d_6$-DMSO): δ (ppm) 1.52 (m, 1H); 1.65 (m, 2H); 1.75 (m, 1H); 1.95 (m, 1H); 2.0–2.2 (m, 2H); 2.06 (m, 1H); 2.1 (m, 1H); 2.23 (s, 3H); 2.46 (m, 1H); 2.69 (m, 1H); 2.82 (m, 1H); 2.9 (m, 1H); 2.92 (m, 1H); 2.96 (m, 1H); 3.07 (s, 3H); 3.2 (m, 1H); 3.48 (m, 1H); 3.78 (m, 1H); 4.14 (bd, 1H); 4.35 (bd, 1H); 4.54 (bd, 1H); 6.69 (td, 1H); 6.81 (dd, 1H); 7.04 (dd, 1H); 7.54 (s, 2H); 7.8 (s, 1H).

EXAMPLE 28

1-(4-Fluoro-2-methyl-phenyl)-4-((8aS)-6-oxo-hexahydro-pyrrolo[1,2-a]pyrazin-2-yl)piperidine-2-carboxylic acid (3,5*bis-trifluoromethyl-benzyl)-methyl-amide hydrochloride (syn)

Hydrochloric acid (1M in Et2O—21.5 µL) was added to a solution of example 27 (12 mg) in dry Et2O (1 mL) previously cooled to 0° C. under a nitrogen atmosphere. The resulting mixture was stirred at 0° C. for 30 minutes. The solution was concentrated in vacuo. The residue was triturated with pentane (2×1 mL) to give the title compound as a white solid (12 mg).

NMR (d$_6$-DMSO): δ (ppm) 1.62 (m, 1H); 1.87 (m, 1H); 1.91 (b, 1H); 2.06 (b, 1H); 2.1–2.4 (m, 2H); 2.16 (m, 1H); 2.25 (s, 3H); 2.5 (m, 1H); 2.56 (m, 1H); 2.6 (m, 1H); 2.7–3.8 (m, 5H); 2.95 (m, 1H); 3.1 (m, 1H); 3.9 (bd, 1H); 3.96 (bd, 1H); 4.24 (bm, 1H); 4.67 (bd, 1H); 6.81 (td, 1H); 6.82 (dd, 1H); 7.05 (dd, 1H); 7.54 (s, 2H); 7.81 (s, 1H); MS (ES/+) m/z=615 [M+H−HCl]$^+$.

PHARMACY EXAMPLES

Pharmacy Examples

A. Tablets

| | |
|---|---|
| Active ingredient | 10.0 mg |
| PVP | 9 mg |
| Microcrystalline Cellulose | 266 mg |
| Sodium Starch Glycolate | 12 mg |
| Magnesium Stearate | 3 mg |
| Active ingredient | 50 mg |
| PVP | 9 mg |
| Microcrystalline Cellulose | 226 mg |
| Sodium Starch Glycolate | 12 mg |
| Magnesium Stearate | 3 mg |

The active ingredient is blended with the other excipients. The blend can be compressed to form tablets using appropriate punches. The tablets can be coated using conventional techniques and coatings.

B. Capsules

| | |
|---|---|
| Active ingredient | 25.0 mg (1–100 mg) |
| Microcrystalline Cellulose | qs |

The active ingredient is blended with microcrystalline cellulose and then filled into suitable capsules.

C) Injection

| | |
|---|---|
| Active ingredient | 2–20 mg/mL |
| Buffer solution pH 3.5 (3.0–4.0) suitable for injection (e.g. citrate buffer in sterile water for injection or NaCl 0.9%) | qs to 10 mL |

The formulation may be packaged in glass or plastic vials or ampules. The formulation may be administered by bolus injection or infusion, e.g. after dilution with D5W or 0.9% NaCl.

The affinity of the compound of the invention for NK$_1$ receptor was determined using the NK$_1$ receptor binding affinity method measuring in vitro by the compounds' ability to displace [3H]—substance P (SP) from recombinant human NK$_1$ receptors expressed in Chinese Hamster Ovary (CHO) cell membranes. The affinity values are expressed as negative logarithm of the inhibition constant (Ki) of displacer ligands (pKi).

The pKi values obtained as the average of at least two determinations with representative compounds of the invention are within the range of 9.40 to 11.00.

The invention claimed is:
1. A compound of formula (I)

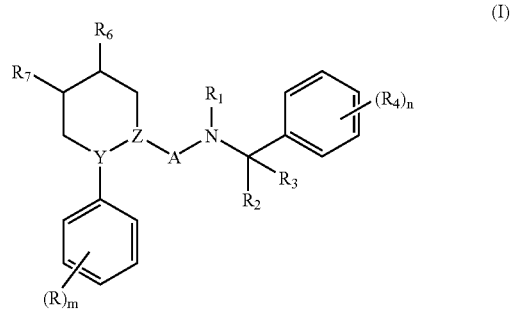

wherein
R is halogen or C$_{1-4}$ alkyl;
R$_1$ is C$_{1-4}$ alkyl;
R$_2$ or R$_3$ independently are hydrogen or C$_{1-4}$ alkyl;
R$_4$ is trifluoromethyl, C$_{1-4}$ alkyl, C$_{1-4}$ alkoxy, trifluoromethoxy or halogen;
R$_5$ represents hydrogen, C$_{1-4}$ alkyl or C$_{3-7}$ cyoloalkyl;
R$_6$ is hydrogen and R$_7$ is a radical of formula (W):

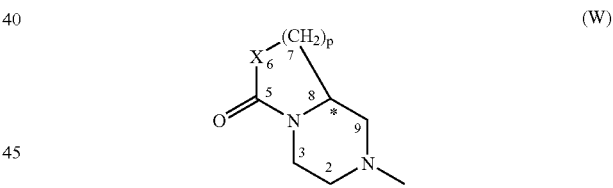

or R$_6$ is a radical of formula (W) and R$_7$ is hydrogen;
X is CH$_2$, NR$_5$ or O;
Y is Nitrogen and Z is CH or Y is CH and Z is Nitrogen;
A is C(O) or S(O)q, provided that when Y is nitrogen and Z is CH, A is not S(O)$_q$;
m is zero or an integer from 1 to 3;
n is an integer from 1 to 3;
p and q are independently an integer from 1 to 2;
or a pharmaceutically acceptable salt or hydrate thereof.

2. A compound as claimed in claim 1 R$_6$ is hydrogen, R$_7$ is a radical of formula (W) and Y is CH and Z is nitrogen.

3. A compound as claimed in claim 1 wherein A is C(O).

4. A compound as claimed in claim 1 wherein X is CH$_2$.

5. A compound as claimed in claim 1 wherein p is 1.

6. A compound as claimed in claim 1 wherein each R$_4$ is independently trifluoromethyl group or halogen and n is 2.

7. A compound as claimed in claim 1 wherein each R is independently a halogen or a C$_{1-4}$ alkyl group, wherein m is 0, 1 or 2.

8. A compound as claimed in claim 1 wherein $R_6$ is hydrogen, $R_7$ is a radical of formula (W) and Y is CH and Z is nitrogen.

9. A compound as claimed in claim 1 wherein $R_6$ is hydrogen, $R_7$ is a radical of formula (W) and Y is CH and Z is nitrogen.

10. A compound selected from:
2-(R)-(4-Fluoro-2-methyl-phenyl)-4-(S)-(6-oxo-hexahydro-pyrrolo[1,2-a]-pyrazin-2-yl)-piperidine-1-carboxylic acid (3,5-bis-trifluoromethyl-benzyl)-methylamide;
2-(R)-(4-Fluoro-2-methyl-phenyl)-4-(S)-(6-oxo-hexahydro-pyrrolo[1,2-a]-pyrazin-2yl)-1-piperidine-1-carboxylic acid[1-(R)-(3,5-bis-trifluoromethyl-phenyl)-ethyl]-methylamide;
1-(4-Fluoro-2-methyl-phenyl)-4-(6-oxo-hexahydro-pyrrolo[1,2-a]pyrazin-2-yl)-piperidine-2-carboxylic acid (3,5-bis-trifluoromethyl-benzyl)-methyl-amide;
and enantiomers, diastereoisomers, and pharmaceutically acceptable salts or hydrates thereof.

11. A compound selected from:
2-(R)-(4-Fluoro-2-methyl-phenyl)-4-(S)-((8aS)-6-oxo-hexahydro-pyrrolo[1,2-a]-pyrazin-2yl)-piperidine-1-carboxylic acid [1-(R)-(3,5-bis-trifluoromethyl-phenyl)-ethyl]-methylamide;
2-(R)-(4-Fluoro-2-methyl-phenyl)-4-(S)-((8aR)-6-oxo-hexahydro-pyrrolo[1 2-a]-pyrazin-2-yl)-piperidine-1-carboxylic acid [1-(R)-(3,5-bis-trifluoromethyl-phenyl)ethyl]-methylamide;
and amorphous and crystalline forms thereof and pharmaceutically acceptable salts or hydrates thereof.

12. A compound as claimed in claim 1 wherein $R_6$ is a radical of formula (W), $R_7$ is a hydrogen and Y is nitrogen and Z is CH.

13. A compound as claimed in claim 1 wherein $R_6$ is a radical of formula (W), $R_7$ is a hydrogen and Y is nitrogen and Z is CH, A is C(O) and X is $CH_2$.

14. A compound as claimed in claim 1 wherein $R_6$ is a radical of formula (W), $R_7$ is a hydrogen, Y is nitrogen, Z is CH, A is C(O), X is $OH_2$, R is independently a halogen or a $C_{1-4}$ alkyl group, $R_4$ is a trifluoromethyl group, m is 1 or 2, n is 2 and p is 1.

15. 2-(R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide and enantiomers, diastereoisomers, and pharmaceutically acceptable salts or hydrates thereof.

16. 2-(R)-(4-Fluoro-2-methyl-phenyl)-4-(S)-((8aS-6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide hydrochloride.

17. 2-(R)-(4-Fluoro2-methyl-phenyl)-4-(S)-((8aS-6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide hydrochloride as anhydrous crystalline form.

18. A pharmaceutical composition comprising a compound as claimed in claim 1 in admixture with one or more pharmaceutically acceptable carriers or excipients.

19. The pharmaceutical composition as claimed in claim 18, further comprising a serotonin reuptake inhibitor.

20. The pharmaceutical composition as claimed in claim 19, wherein said serotonin reuptake inhibitor is selected from fluvoxamine, citalopram, femoxetine, fluvoxamine, paroxetine, indalpine, sertraline and zimeldine.

21. The pharmaceutical composition as claimed in claim 18, further comprising a dopaminergic antidepressant.

22. The pharmaceutical composition as claimed in claim 21, wherein said dopaminergic antidepressant is selected from bupropion and amineptine.

23. The pharmaceutical composition as claimed in claim 18, further comprising a 5HT3 antagonist.

24. The pharmaceutical composition as claimed in claim 23, wherein said 5HT3 antagonist is selected from ondansetron, granisetron and metoclopramide.

25. A method for the treatment of a depressive state or anxiety in man, comprising administering an effective amount of a compound according to claim 1.

26. The method according to claim 25, wherein said depressive state is selected from
bipolar depression,
unipolar depression.
single or recurrent major depressive episodes,
recurrent brief depression with or without psychotic features, catatonic features, melancholic features, weight loss, atypyical features,
anxious depression,
cyclothymic or postpartum onset,
dysthymic disorder with early or late onset and with or without atypical features;
neurotic depression;
post traumatic stress disorders;
social phobia;
dementia of the Alzheimer's type, with early or late onset, with depressed mood;
vascular dementia with depressed mood;
mood disorders induced by alcohol, amphetamines, cocaine, hallucinogens, inhalants, opioids, phencyclidine, sedatives, hypnotics, and anxiolytics;
schizoaffective disorder at the depressed type;
adjustment disorder with depressed mood; and
major depressive disorders resulting from a general medical condition.

27. The method as claimed in claim 25, wherein said compound is 2-(R)-(4-Fluoro-2-methyl-phenyl)-4-(S)-((8aS-6-oxo-hexahydro-pyrrolo[1,2-a]-pyrazin-2-yl)-piperidine-1-carboxylic acid[1-( R)-(3,5-bis-trifluoromethyl-phenyl)-ethyl]-methylamide hydrochloride.

28. The method as claimed in claim 25, wherein said anxieity is an anxiety disorder selected from
panic disorders with or without agoraphobia,
agoraphobia,
phobias,
obsessive-compulsive disorder,
post-traumatic stress disorders.
generalized anxiety disorders,
acute stress disorders, and
mixed anxiety-depression disorders.

29. The method as claimed in claim 25, wherein said compound is
2-( R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide;
or an enantiomer, diastereoisomer or pharmaceutically acceptable salt or hydrate thereof.

30. The method as claimed in claim 25, further comprising administering an effective amount of a serotonin reuptake inhibitor.

31. The method as claimed in claim 30, wherein said serotonin reuptake inhibitor is selected from fluoxetine, citalopram, femoxetine, fluvoxamine, paroxetine, indalpine, sertraline and zimeldine.

32. The method as claimed in claim 25 further comprising administering an effective amount of a dopaminergic antidepressant.

33. The method as claimed in claim 32, wherein said dopaminergic antidepressant is selected from bupropion and amineptine.

34. A method for the treatment of a major depressive disorder in man comprising administering an effective amount of 2-(R)-(4-Fluoro-2-methyl-phenyl)-4-(S)-(6-oxo-hexahydro-pyrrolo[1,2-a]-pyrazin-2-yl)-piperidine 1-carboxylic acid[1-(R)-(3,5-bis-trifluoromethyl-phenyl)-ethyl]-methylamide, or an enantiomer, diastereoisomer, or pharmaceutically acceptable salt or hydrate thereof.

35. The method as claimed in claim 34, wherein said major depressive disorder is selected from bipolar depression and unipolar depression.

36. The method as claimed in claim 34, further comprising administering an effective amount of a serotonin reuptake inhibitor selected from fluoxetine, citalopram, femoxetine, fluvoxamine, paroxetine, indalpine, sertraline and zimeldine.

37. The method as claimed in claim 34, further comprising administering an effective amount of a dopaminergic antidepressant selected from bupropion and amineptine.

38. A method for the treatment of anxiety in man comprising administering an effective amount of 2-(R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide, or an enantiomer, diastereoisomer, or pharmaceutically acceptable salt or hydrate thereof.

39. The method as claimed in claim 38, further comprising administering an effective amount of a serotonin reuptake inhibitor selected from fluoxetine, citalopram, femoxetine, fluvoxamine, paroxetine, indalpine. sertraline and zimeldine.

40. The method as claimed in claim 38, further comprising administering an effective amount of a dopaminergic antidepressant selected from bupropion and amineptine.

41. A method for the treatment of panic disorder in man comprising administering an effective amount of 2-(R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide, or an enantiomer, diastereoisomer, or pharmaceutically acceptable salt or hydrate thereof.

42. A method for the treatment of emesis in a mammal comprising administering an effective amount of a compound as claimed in claim 1.

43. The method as claimed in claim 42, wherein said mammal is man.

44. The method as claimed in claim 42. wherein said emesis is delayed emesis.

45. The method as claimed in claim 42, wherein said emesis is anticipatory emesis.

46. The method as claimed in claim 42, wherein said emesis is induced by cancer chemotherapeutic agents.

47. The method as claimed in claim 46, wherein said cancer chemotherapeutic agent is selected from cyclophosphamide, carmustine, lomustine, chlorambucil, dactinomycin, doxorubicin, mitomycin-C, bleomycin, cytarabine, methotrexate, 5-fluorouracil, etoposide, vinblastine, vincristine, cisplatin, dacarbazine, procarbazine, hydroxyurea and combinations thereof.

48. The method as claimed in claim 42, wherein said emesis is induced by radiation sickness or radiation therapy.

49. The method as claimed in claim 42, wherein said emesis is induced by pregnancy.

50. The method as claimed in claim 42, wherein said emesis is induced by post-operative sickness.

51. The method as claimed in claim 42, wherein said emesis is induced by migraine.

52. The method as claimed in claim 42, wherein said emesis is induced by opioid analgesics.

53. The method as claimed in claim 42, further comprising administering an effective amount of a 5HT3 antagonist.

54. The method as claimed in claim 53, wherein said 5HT3 antagonist is selected from ondansetron, granisetron and metoclopramide.

55. The method as claimed in claim 42, wherein said compound is 2-(R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide or an enantiomer, diastereoisomer or pharmaceutically acceptable salt or hydrate thereof.

56. The method as claimed in claim 55, further comprising administering an effective amount of a 5HT3 antagonist selected from ondansetron, granisetron and metoclopramide.

57. A method for the treatment of emesis in man comprising administering an effective amount of 2-(R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide, or an enantiomer, diastereoisomer, or pharmaceutically acceptable salt or hydrate thereof.

58. A method for the treatment of a sleep disorder in man comprising administering an effective amount of a compound as claimed in claim 1.

59. A method for the treatment of dependence on a substance selected from nicotine, alcohol, caffeine, phencyclidine phencyclidine-like compounds, opiates, benzodiazepines, cocaine, sedative drugs, hypnotic drugs, amphetamines, dextroamphetamine, methamphetamine, and combinations thereof; in man, comprising administering an effective amount of a compound as claimed in claim 1.

60. A method for the treatment of a major depressive disorder in man comprising administering an effective amount of 2-(R)-(4-Fluoro-2-methyl-phenyl)-4-(S)-((8aS-6-oxo-hexahydro-pyrrolo[1,2a]-pyrazin-2-yl)-piperidine-1-carboxylic acid[1-(R)-(3,5-bis-trifluoromethyl-phenyl)-ethyl]-methylamide hydrochloride.

61. A method for the treatment of anxiety in man comprising administering an effective amount of 2-(R)-(4-Fluoro-2-methyl-phenyl)-4-(S)-((8aS-6-oxo-hexahydro-pyrrolo[1,2-a]-pyrazin-2-yl)-piperidine-1-carboxylic acid [1-(R)-(3,5-bis-triufluoromethyl-phenyl)-ethyl]-methylamide hydrochloride.

62. A method for the treatment of panic disorder in man comprising administering an effective amount of 2-(R)-(4-Fluoro-2-methyl-phenyl)-4-(S)-((8aS-6-oxo-hexahydro-pyrrolo[1,2-a]-pyrazin-2-yl)-piperidine-1-carboxyl acid[1-(R)-(3,5-bis-trifluoromethyl-phenyl)-ethyl]-methylamide hydrochloride.

63. The method as claimed in claim 25, wherein said compound is 2-(R)-(4-Fluoro-2-methyl-phenyl)-4-(S)-((8aR)-6-oxo-hexahydro-pyrrolo[1 2-a]-pyrazin-2-yl)-piperidine-1-carboxylic acid[1-(R)-(3,5-bis-trifluoromethyl-phenyl)-ethyl]-methylamide hydrochloride.

64. A method for the treatment of a major depressive disorder in man comprising administering an effective amount of 2-(R)-(4-Fluoro-2-methyl-phenyl)-4-(S)-((8aR)-6-oxo-hexahydro-pyrrolo[1,2-a]-pyrazin-2-yl)-piperidine- 1-carboxylic acid[1-(R)-(3,5-bis-trifluoromethyl-phenyl)-ethyl]-methylamide hydrochloride.

65. A method for the treatment of anxiety in man comprising administering an effective amount of 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride.

66. A method for the treatment of panic disorder in man comprising administering an effective amount of 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride.

67. The method as claimed in claim 58, wherein said compound is 2-(R)-(4-Fluoro-2-methyl-phenyl)-4-(S)-(6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide, or an enantiomer, diastereoisomer, or pharmaceutically acceptable salt or hydrate thereof.

68. A method for the treatment of a sleep disorder in man comprising administering an effective amount of 2-(R)-(4-Fluoro-2-methyl-phenyl)-4-(S)-((8aS-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride.

69. A method for the treatment of a sleep disorder in man comprising administering an effective amount of 2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide hydrochloride.

70. A process for the preparation of a compound as claimed in claim 1 comprising reacting a compound of formula (II) wherein $R_8$ is =O and $R_9$ is hydrogen or $R_8$ is hydrogen and $R_9$ is =O

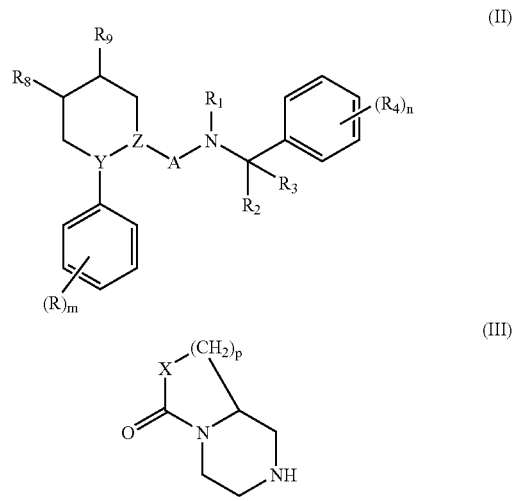

with compound of formula (III) or a salt thereof in the presence of a suitable metal reducing agent to prepare a compound of formula (I) followed where necessary or desired by one or more of the following steps:

i) removal of any protecting group;

ii) isolation of the compound of formula (I) as a salt or a hydrate thereof;

iii) separation of a compound of formula (I) or salt or hydrate thereof into the enantiomers thereof.

71. 2-(R)-(4-Fluoro-2-methyl-phenyl)-4-(S)-((8aR)-6-oxo-hexahydro-pyrrolo[1,2-a]-pyrazin-2-yl)-piperidine-1-carboxyl acid[1-(R)-(3,5-bis-trifluoromethyl-phenyl)-ethyl]-methylamide hydrochloride.

* * * * *

UNITED STATES PATENT AND TRADEMARK OFFICE
CERTIFICATE OF CORRECTION

PATENT NO. : 7,189,713 B2
APPLICATION NO. : 10/502255
DATED : March 13, 2007
INVENTOR(S) : Alvaro et al.

It is certified that error appears in the above-identified patent and that said Letters Patent is hereby corrected as shown below:

Column 57, claim 10, line 13 should read:

-- dro-pyrrolo[1,2-a]pyrazin-2yl)-piperidine-1-car --

Column 57, claim 14, line 41 should read:

-- CH, A is C(O), X is $CH_2$, R is independently a halogen or --

Column 57, claim 17, line 53 should read:

-- 2-(R)-(4-Fluoro-2-methyl-phenyl)-4-(S)-((8aS-6-oxo- --

Column 57, claim 19, line 64 should read:

-- from fluoxamine, citalopram, fcmoxetine, fluvoxamine, --

Column 58, claim 26, line 33 should read:

-- schizoaffective disorder of the depressed type --

Column 60, claim 61, line 50 should read:

-- [1-(R)-(3,5-bis-trifluoromethyl-phenyl)-ethyl]- --

UNITED STATES PATENT AND TRADEMARK OFFICE
CERTIFICATE OF CORRECTION

PATENT NO. : 7,189,713 B2
APPLICATION NO. : 10/502255
DATED : March 13, 2007
INVENTOR(S) : Alvaro et al.

It is certified that error appears in the above-identified patent and that said Letters Patent is hereby corrected as shown below:

Column 62, claim 71, line 36 should read:

-- carboxylic acid[1-(R)-(3,5-bis-trifluoromethyl-phenyl)- --

Signed and Sealed this

Ninth Day of October, 2007

JON W. DUDAS
*Director of the United States Patent and Trademark Office*